US006815211B1

(12) United States Patent
Blazewicz et al.

(10) Patent No.: US 6,815,211 B1
(45) Date of Patent: Nov. 9, 2004

(54) OXYGEN MONITORING METHODS AND APPARATUS (I)

(75) Inventors: Perry R. Blazewicz, Tacoma, WA (US); Leslie E. Mace, Mercer Island, WA (US); Jerry R. Apperson, Lake Forest Park, WA (US); Gamal-Eddin Khalil, Redmond, WA (US)

(73) Assignee: NTC Technology, Wilmington, DE (US)

(*) Notice: Subject to any disclaimer, the term of this patent is extended or adjusted under 35 U.S.C. 154(b) by 0 days.

(21) Appl. No.: 09/128,897

(22) Filed: Aug. 4, 1998

(51) Int. Cl.[7] ............................................. G01N 21/75
(52) U.S. Cl. ...................... 436/166; 422/55; 422/82.06; 422/83; 422/82.05; 436/68; 436/164; 436/172; 427/2.13
(58) Field of Search .......................... 422/82.06, 82.07, 422/82.11, 83, 87, 55; 436/164, 172, 800, 68, 166; 427/2.13

(56) References Cited

U.S. PATENT DOCUMENTS

| 2,950,237 A | 8/1960 | Sharp et al. |
| 3,429,667 A | 2/1969 | Hart et al. |
| 3,612,866 A | 10/1971 | Stevens |

(List continued on next page.)

FOREIGN PATENT DOCUMENTS

| WO | WO 00/13003 | 3/2000 |
| WO | WO 01/08554 A1 | 2/2001 |

OTHER PUBLICATIONS

Bacon, J. R., Demas, J. N.; "Determination of Oxygen Concentrations by Luminescence Quenching of a Polymer-Immobilized Transition–Metal Complex;" pp. 2780–2785, *Analytical Chemistry*, vol. 59, No. 23, Dec. 1, 1987.

Gewehr, P. M., Delphy, D. T.; "Optical oxygen sensor based on phosphorescence lifetime quenching and employing a polymer immobilised metalloporphyrin probe, Part 1 Theory and instrumentation;" pp. 1–10, *Medical & Biological Engineering & Computing*, Jan. 1993.

(List continued on next page.)

*Primary Examiner*—Jill Warden
*Assistant Examiner*—Dwayne K Handy
(74) *Attorney, Agent, or Firm*—TraskBritt

(57) ABSTRACT

Apparatus or systems which employ luminescence quenching to produce an oxygen concentration indicative signal. Components of such systems include: (1) an airway adapter, sampling cell, or the like having a sensor which is excited into luminescence with the luminescence decaying in a manner reflecting the concentration of oxygen in gases flowing through the airway adapter or other flow device; (2) a transducer which has a light source for exciting a luminescable composition in the sensor into luminescence and a light sensitive detector for converting energy emitted from the luminescing composition as that composition is quenched into an electrical signal indicative of oxygen concentration in the gases being monitored; and (3) sub-systems for maintaining the sensor temperature constant and for processing the signal generated by the light sensitive detector. Sensors for systems of the character just described, methods of fabricating those sensors, and methods for installing the sensors in the flow device.

16 Claims, 16 Drawing Sheets

U.S. PATENT DOCUMENTS

| | | | |
|---|---|---|---|
| 3,725,658 | A | 4/1973 | Stanley et al. |
| 3,734,691 | A | 5/1973 | Kukla et al. |
| 3,734,862 | A | 5/1973 | Maulding |
| 3,830,222 | A | 8/1974 | Chance |
| 4,003,707 | A | 1/1977 | Lübbers et al. |
| 4,223,226 | A | 9/1980 | Quick et al. |
| 4,245,507 | A | 1/1981 | Samulski |
| 4,272,485 | A | 6/1981 | Lübbers |
| 4,321,057 | A | 3/1982 | Buckles |
| 4,399,099 | A | 8/1983 | Buckles |
| 4,437,772 | A | 3/1984 | Samulski |
| 4,476,870 | A | 10/1984 | Peterson et al. |
| RE31,832 | E | 2/1985 | Samulski |
| RE31,879 | E | 5/1985 | Lü bbers et al. |
| 4,542,987 | A | 9/1985 | Hirschfeld |
| 4,568,518 | A | 2/1986 | Wolfbeis et al. |
| 4,587,101 | A | 5/1986 | Marsoner et al. |
| 4,608,344 | A | 8/1986 | Carter et al. |
| 4,652,143 | A | 3/1987 | Wickersheim et al. |
| 4,657,736 | A | 4/1987 | Marsoner et al. |
| 4,682,895 | A | 7/1987 | Costello |
| 4,730,112 | A | 3/1988 | Wong |
| 4,750,837 | A | 6/1988 | Gifford et al. |
| 4,752,115 | A | 6/1988 | Murray, Jr. et al. |
| 4,775,514 | A | 10/1988 | Barnikol et al. |
| 4,810,655 | A | 3/1989 | Khalil et al. |
| 4,822,899 | A | 4/1989 | Groves et al. |
| 4,849,172 | A | 7/1989 | Yafuso et al. |
| 4,861,727 | A | 8/1989 | Hauenstein et al. |
| RE33,064 | E | 9/1989 | Carter et al. |
| 4,892,383 | A | 1/1990 | Klainer et al. |
| 4,892,941 | A | 1/1990 | Dolphin et al. |
| 4,895,156 | A | 1/1990 | Schulze |
| 4,919,891 | A | 4/1990 | Yafuso et al. |
| 4,954,318 | A | 9/1990 | Yafuso et al. |
| 4,968,632 | A | 11/1990 | Brauer et al. |
| 4,973,718 | A | 11/1990 | Buchler et al. |
| 5,012,809 | A | 5/1991 | Shulze |
| 5,030,420 | A * | 7/1991 | Bacon et al. ............ 422/82.07 |
| 5,034,189 | A | 7/1991 | Cox et al. |
| 5,043,286 | A | 8/1991 | Khalil et al. |
| 5,045,282 | A | 9/1991 | Kritzman et al. |
| 5,047,350 | A | 9/1991 | Switalski et al. |
| 5,061,076 | A | 10/1991 | Hurley |
| 5,081,041 | A * | 1/1992 | Yafuso et al. ................. 436/68 |
| 5,094,959 | A | 3/1992 | Allen et al. |
| 5,098,659 | A | 3/1992 | Yim et al. |
| 5,127,077 | A | 6/1992 | Iyer et al. |
| 5,128,102 | A | 7/1992 | Kaneko et al. |
| 5,152,287 | A | 10/1992 | Kane |
| 5,173,432 | A | 12/1992 | Lefkowitz et al. |
| 5,188,108 | A | 2/1993 | Secker |
| 5,194,391 | A | 3/1993 | Nauze et al. |
| 5,233,194 | A | 8/1993 | Mauze et al. |
| 5,234,835 | A | 8/1993 | Nestor et al. |
| 5,242,835 | A | 9/1993 | Jensen |
| 5,244,810 | A | 9/1993 | Gottlieb |
| 5,252,494 | A | 10/1993 | Walt |
| 5,262,192 | A | 11/1993 | Nelson et al. |
| 5,285,783 | A | 2/1994 | Secker |
| 5,285,784 | A | 2/1994 | Seeker |
| 5,308,581 | A | 5/1994 | Lippitsch et al. |
| 5,308,771 | A | 5/1994 | Zhou et al. |
| 5,326,585 | A | 7/1994 | Nelson et al. |
| 5,344,810 | A | 9/1994 | Hirata et al. |
| 5,511,547 | A * | 4/1996 | Markle et al. .............. 128/633 |
| 5,517,313 | A | 5/1996 | Colvin, Jr. |
| 5,670,097 | A * | 9/1997 | Duan et al. ................ 422/68.1 |
| 5,718,842 | A * | 2/1998 | Papkovsky et al. .... 252/301.16 |
| 5,804,048 | A * | 9/1998 | Wong et al. ................ 204/403 |
| 5,830,138 | A * | 11/1998 | Wilson ........................ 436/68 |
| 5,910,661 | A | 6/1999 | Colvin, Jr. |
| 5,997,818 | A * | 12/1999 | Hacker et al. ............. 422/68.1 |
| 6,015,715 | A * | 1/2000 | Kirschner et al. .......... 436/166 |
| 6,402,698 | B1 | 6/2002 | Mault |

OTHER PUBLICATIONS

Gewehr, P. M. Delpy, D. T.; "Optical oxygen sensor based on phosphorescence lifetime quenching and employing a polymer immobilised metalloporphyrin probe, Part 2 Sensor membranes and results;" pp. 11–21, *Medical & Biological Engineering & Computing* Jan. 1993.

Kolle, C., O'Leary, P.; "Optical Oxygen Sensor for Breath-Gas Analysis;" *Report Institute for Chemical and Optical Sensors*; Report No: COS 95.001, Feb. 1995.

H. S. Voraberger et al.; Novel oxygen optrode withstanding autoclavation: technical solutions and performance; pp. 1–7, *Sensors and Actuator B 3679*, 2000.

Ammann, "What exactly is 'permeation'?" Dräger Review 82, pp. 13–16 (Oct. 1998).

U.S. Environmental Protection Agency (EPA) publication entitled "SITE Technology Capsule: ZENON Environmental, Inc. Cross–Flow Pervaporation System," Aug. 1995.

* cited by examiner

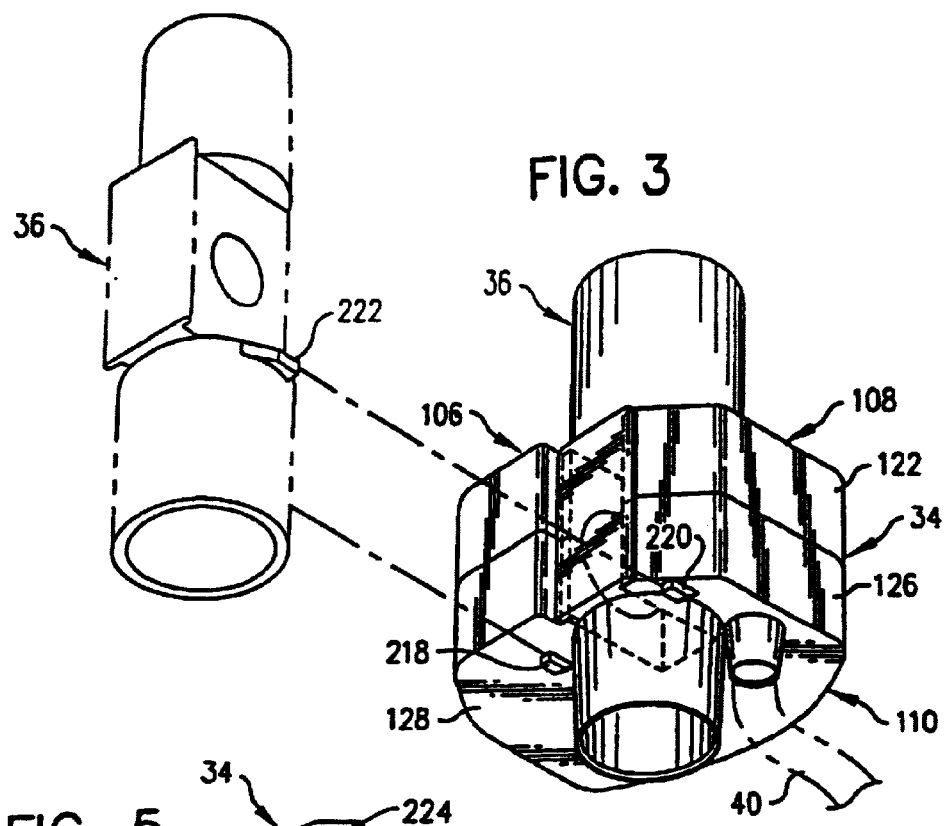
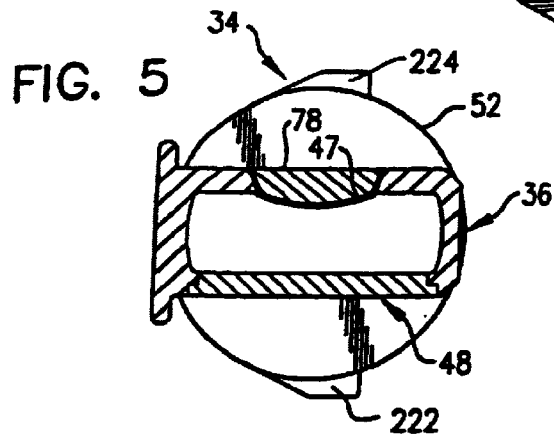
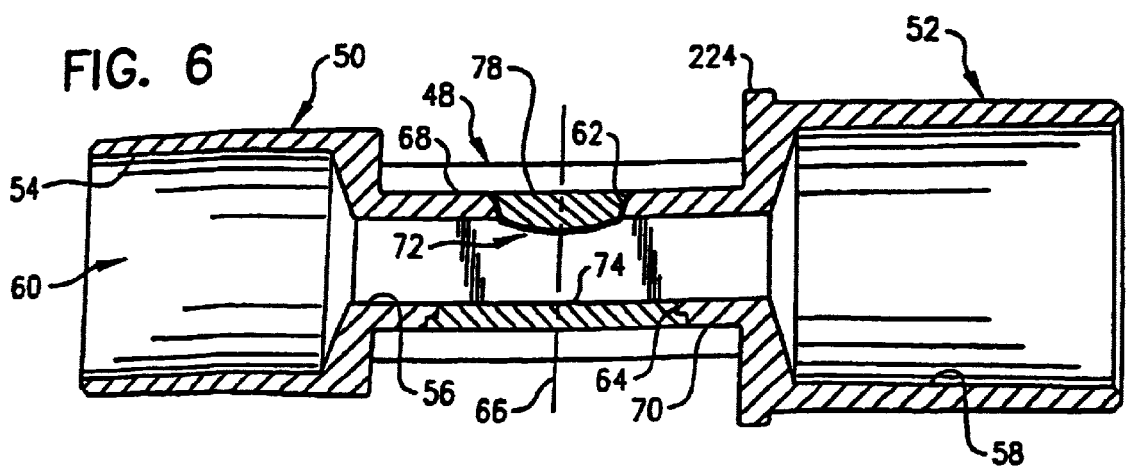

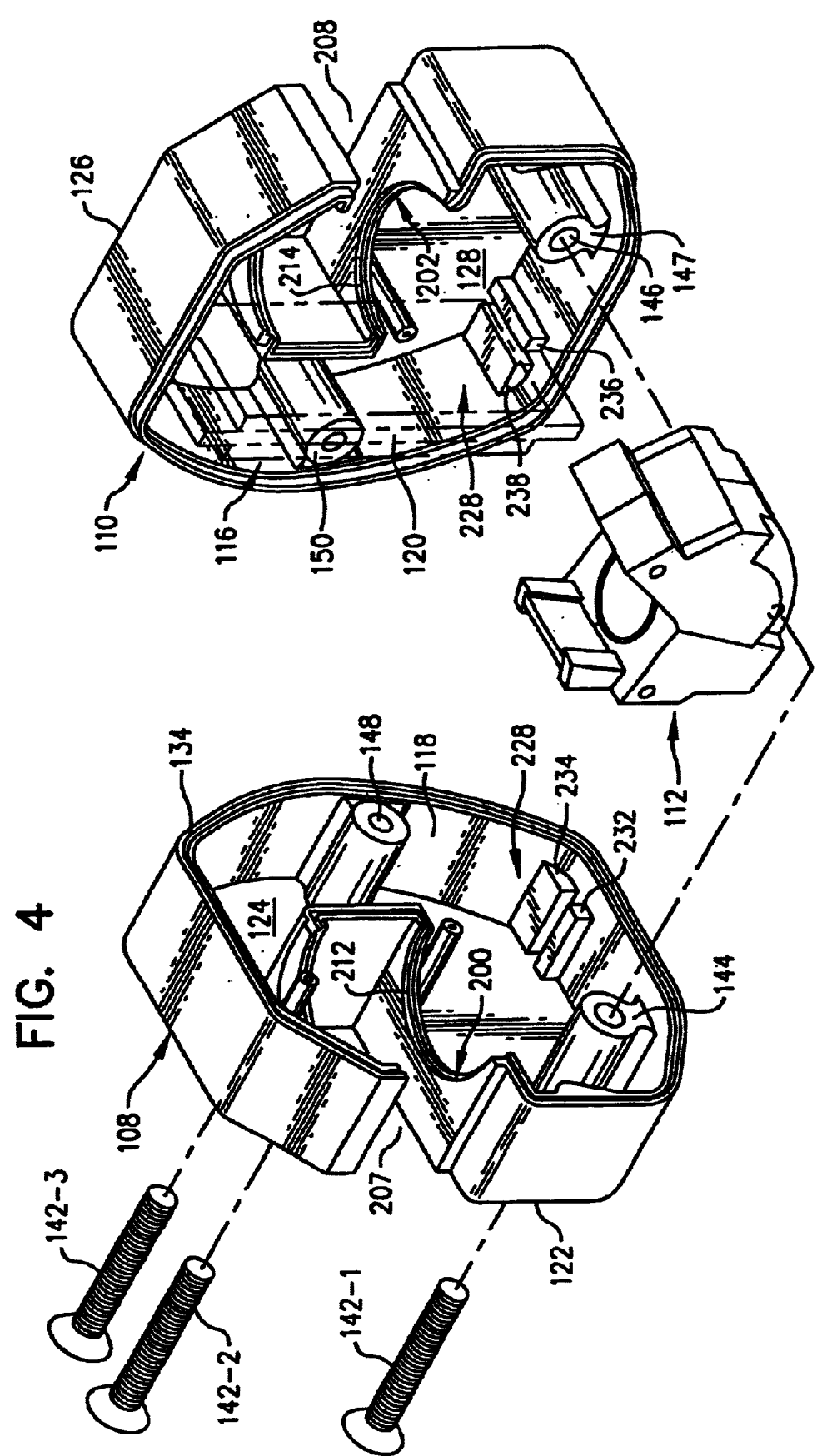

STEP 1

STEP 2

STEP 3

STEP 4

OXYGEN MONITORING METHODS AND APPARATUS (I)

TECHNICAL FIELD OF THE INVENTION

The present invention relates to the monitoring of oxygen concentration and, more particularly, to novel, improved methods and apparatus for monitoring the concentration of oxygen in respiratory and other gases and to components of and controls for apparatus as just characterized.

In another aspect, the present invention relates to methods of manufacturing airway adapters designed for use in on-airway applications of the invention.

In a third aspect, the present invention relates to novel sensors which include an oxygen quenchable luminescable compound and methods for manufacturing sensors of the character.

BACKGROUND OF THE INVENTION

The most common cause of anesthetic and ventilator related mortality and morbidity is inadequate delivery of oxygen to a patient's tissues. Therefore, the monitoring of static inspired oxygen concentration has long been a safety standard of practice to ensure detection of hypoxic gas delivery to patients undergoing surgery and to those on mechanical ventilators and receiving supplemental oxygen therapy. However, monitoring the static inspired fraction of inhaled oxygen does not always guarantee adequate oxygen delivery to the tissues because it is the alveolar oxygen concentration that eventually enriches the blood delivered to the cells.

It is this alveolar gas phase that is interfaced with pulmonary perfusion which, in turn, is principally responsible for controlling arterial blood gas levels. It is very important that the clinician know the blood gas levels (partial pressure) of oxygen ($pO_2$) and carbon dioxide ($pCO_2$) as well as the blood pH. Blood gas levels are used as an indication of incipient respiratory failure and in optimizing the settings on ventilators. In addition, blood gas levels can detect life-threatening changes in an anesthetized patient undergoing surgery.

The traditional method for obtaining arterial blood gas values is highly invasive. A sample of arterial blood is carefully extracted and the partial pressure of the gases is measured, using a blood gas analyzer. Unfortunately, arterial puncture has inherent limitations: (1) arterial puncture requires a skilled health care provider and it carries a significant degree of patient discomfort and risk, (2) handling the blood is a potential health hazard to the health care provider, (3) significant delays are often encountered before results are obtained, and (4) measurements can only be made intermittently.

Non-invasive methods for estimating blood gas levels are available. Such methods include the use of capnography ($CO_2$ analysis). These methods employ fast gas analyzers at the patient's airway and give a graphic portrayal of breath-by-breath gas concentrations and, therefore, can measure the peak exhaled (end tidal) concentrations of the respective respired gases. Although gradients can occur between the actual arterial blood gas levels and the end tidal values, this type of monitoring is often used as a first order approximation of the arterial blood gas values.

Other techniques have been utilized for assessing patient blood gas levels with mixed results. Transcutaneous sensors measure tissue $pO_2$ and $pCO_2$ diffused through the heated skin surface. This type of sensor has a number of practical limitations including a slow speed of response and difficulty of use.

Pulse oximetry is widely used to measure the percentage of hemoglobin that is saturated with oxygen. Unfortunately, it does not measure the amount of dissolved oxygen present nor the amount of oxygen carried by the blood when hemoglobin levels are reduced. This is important because low hemoglobin levels are found when there is a significant blood loss or when there is insufficient red blood cell information. In addition, pulse oximeter readings are specific to the point of contact, which is typically the finger or ear lobe, and may not reflect the oxygen level of vital organs during conditions such as shock or hypothermia.

Oxygraphy measures the approximate concentration of oxygen in the vital organs on a breath-by-breath basis and can quickly detect imminent hypoxemia due to decreasing alveolar oxygen concentration. For example, during hypoventilation, end tidal oxygen concentration changes more rapidly than does end tidal carbon dioxide. During the same conditions, pulse oximetry takes considerably longer to respond. Fast oxygen analysis (oxygraphy) can also readily detect inadvertent administration of hypoxic gas mixtures.

Oxygraphy reflects the balance of alveolar $O_2$ available during inspiration minus the $O_2$ uptake secondary to pulmonary perfusion. An increasing difference between inspiratory and end tidal oxygen values is a rapid indicator of a supply/demand imbalance which could be a result of changes in ventilation, diffusion, perfusion and/or metabolism of the patient. This imbalance must be quickly corrected because failure to meet oxygen demand is the most common cause of organ failure, cardiac arrest, and brain damage. Oxygraphy provides the earliest warning of the development of an impending hypoxic episode.

Oxygraphy has also been shown to be effective in diagnosing hypovolemic or septic shock, air embolism, hyperthermia, excessive PEEP, CPPR efficacy, and even cardiac arrest. During anesthesia, oxygraphy is useful in providing a routine monitor of preoxygenation (denitrogenation). It especially contributes to patient safety by detecting human errors, equipment failures, disconnections, misconnections, anesthesia overdoses, and esophageal intubations.

Combining the breath-by-breath analysis of oxygen with the measurement of airway flow/volume as outlined in U.S. Pat. Nos. 5,347,843 and 5,379,650 gives another dimension to the clinical utility of oxygraphy. This combination parameter, known as oxygen consumption ($VO_2$), provides an excellent overall patient status indicator. Adequate cardia output, oxygen delivery, and metabolic activity are all confirmed by oxygen consumption because all of these physiological processes are required for oxygen consumption to take place. Oxygen consumption is also useful in predicting ventilator weaning success.

A metabolic measurement (calorimetry) includes determination of a patient's energy requirements (in calories per day) and respiratory quotient (RQ). Interest in the measurement of caloric requirements has closely paralleled the development of nutritional support. For example, the ability to intravenously provide all the necessary nutrition to critically ill patients has only been accomplished within the last 25 years. Along with the realization that we need to feed patients, has come the need to know how much to feed them, what kind of nutrients (carbohydrates, lipids, protein) to feed them, and in what ratio the nutrients need to be supplied. The only true way to measure the caloric requirements of patients and to provide a non-invasive quality assessment of their response to nutrition is with indirect calorimetry. Airway O2 consumption and $CO_2$ production can be measured non-invasively and provide a basis for the computations needed for a measurement of indirect calorimetry, a direct measurement of the metabolic status of the patient, and the patient's respiratory quotient.

With the above clinical need in mind, it is important to ensure that clinicians have the proper equipment to monitor breath-by-breath oxygen. While there are adequate devices for measuring static levels of oxygen, the measurement of breath-by-breath (fast) airway oxygen concentration requires more sophisticated instruments. Very few of these devices can be directly attached to the patient airway. Instead, most require the use of sampling lines to acquire the gas and send it to a remote site for analysis. Fast airway oxygen monitors are typically large, heavy, fragile instruments that consume considerable power. They must sample airway gases via a small bore plastic tube (sidestream) and remotely detect the oxygen gas as it passes from the airway to the sensor. The problems associated with this type of gas sampling are well known. Gas physics dictates painstaking, careful measurements because water vapor concentration pressure and temperature can vary within the patient's airway and gas sample line. The presence of water and mucous create problems for long term patency of the sample tube. Also, the sample line acts like a low pass filter and affects the fidelity of the measurement. Finally, the pressure variable delay introduced by the sample line creates difficulty in accurately synchronizing the airway flow and oxygen concentration signals required to calculate oxygen consumption.

On-airway (mainstream) monitoring of oxygen has the potential to solve all of the above problems, especially when breath-by-breath monitoring oxygen consumption measurements are to be made. However, most of the available fast oxygen sensors are simply too big, too heavy, too fragile, and/or otherwise not suited to be placed in line with a patient's breathing tube.

There are various other technologies which have been employed in monitoring airway oxygen concentration. Some of the most widely used are electrochemical sensors. These fall into two basic categories: polarographic cells and galvanic cells. These cells produce an electric current proportional to the number of oxygen molecules which diffuse across a membrane. The advantages of these types of sensors are simplicity and low cost. The disadvantages include limited lifetime (chemistry depletes) and slow response (not breath-by-breath). In some cases, these cells have demonstrated sensitivity to certain anesthetic agents, which introduces inaccuracies into the oxygen concentration measurement. Generally, this type of sensor is too large to attach to the patient airway.

There have been a few reported developments where electrochemical cell membranes were improved to enable faster response. There are also silicon micromachined cells using the principle of "Back Cell" electrochemical technology.

Their time response approaches 150 ms but they appear to be subject to the typical problems of this type of cell (i.e., stability and calibration).

Another popular medical oxygen sensor is the paramagnetic type. This sensor uses the strong magnetic property of oxygen as a sensing mechanism. There are two basic types of paramagnetic cells: static and dynamic. The static type is a dumbbell assembly suspended between the poles of a permanent magnet. The magnetic forces of the surrounding oxygen molecules cause a torsional rotation of the dumbbell which can be sensed optically and employed as a measure of oxygen concentration. The dynamic type (see U.S. Pat. No. 4,633,705) uses a magneto-acoustic approach. This requires a gas sample and a reference gas that are mixed within an electromagnetic field. When the field is switched on and off, a pressure signal proportional to the oxygen content is generated. The signal can be detected by a differential microphone. The advantages of the paramagnetic sensor are good linearity and stability. The dynamic type is inherently faster responding than the static type. Both types are subject to mechanical vibration, and the dynamic type has the disadvantage of requiring a reference gas. Neither type is suitable for on-airway applications.

Zirconium oxide cells are frequently used in the automotive industry to measure oxygen concentration. The cell is constructed from a solid electrolyte tube covered by platinum electrodes. When heated to approximately 800 degrees C, a voltage proportional to the logarithm of the ratio between a sample gas and a reference gas is generated. The advantages of this sensor are wide dynamic range, very fast response, and simplicity. The high cell temperature is clearly a disadvantage as is power consumption. Also, the cell is degraded in the presence of anesthetic agents. Clearly, this type of cell cannot be used on a patient airway.

Ultraviolet absorption uses the principle that oxygen exhibits absorption properties in the ultraviolet part of the electromagnetic spectrum (about 147 nm). This technique has been used in several medical applications but has never been reduced to commercial viability. There are numerous technical difficulties which make this a difficult technique for on-airway applications.

Mass spectrometers spread ionized gas molecules into a detectable spectrum according to their mass-to-charge ratios and can accordingly be used to measure oxygen concentration. These instruments are generally large assemblies with ionizing magnets and high vacuum pumps. The advantages of mass spectrometers include high accuracy, multi-gas analysis capability, and rapid response. The disadvantages include high cost, high power consumption, and large size. Mass spectrometers are not suitable for on-airway applications.

Raman scattering spectrometers (as described in U.S. Pat. No. 4,784,486) can also be used to measure oxygen concentration. These devices respond to photons emitted by the collision of a photon with an oxygen molecule. A photon from a high-power laser loses energy to the oxygen molecule and is re-emitted at a lower energy and frequency. The number of photons re-emitted at the oxygen scattering wavelength is proportional to the number of oxygen molecules present. Like mass spectrometers, Raman spectrometers have multi gas analysis capability and rapid response time. Disadvantages include large size and power consumption. Therefore, Raman scattering spectrometers are not suitable for on-airway applications.

Visible light absorption spectrometers (as described in U.S. Pat. Nos. 5,625,189 and 5,570,697) utilize semiconductor lasers that emit light near 760 nm, an area of the spectrum comprised of weak absorption lines for oxygen. With sophisticated circuitry, the laser can be thermally and/or electronically tuned to the appropriate absorption bands. The amount of energy absorbed is proportional to the number of oxygen molecules present. The advantages of this system are precision, fast response, and no consumable or moving parts. The disadvantages include somewhat fragile optical components, sensitivity to ambient temperature shifts, and a long gas sample path length. While there have been attempts to utilize this technology in an on-airway configuration, no commercially viable instruments have so far been available.

Luminescence quenching has also been proposed as a technique for measuring oxygen concentration. In this approach a sensor contacted by the gases being monitored is excited into luminescence. This luminescence is quenched by the oxygen in the monitored gases. The rate of quenching is related to the partial pressure of oxygen in the monitored gases, and that parameter can accordingly be used to provide an indication of the oxygen in the monitored gases. However, nowhere in the prior art are the problems addressed that require resolution for an oxygen concentration monitor employing luminescence quenching to be of any practical value. These problems include: photodegradation-associated and other instabilities of the sensor, low signal level, noise leading to difficulties in assessing the decay of sensor luminescence, acceptably fast response times, thermal drift of the sensor, reproducibility of the sensors, inaccuracies attributable to stray light reaching the data photodetector, and the need for light weight, ruggedness, and low power consumption.

Consequently, there is an existent and continuing need for devices and methods which can be used on-line to obtain a fast (i.e., breath-by-breath), non-invasive measurement of oxygen concentration in respiratory gases.

SUMMARY OF THE INVENTION

There have now been invented and disclosed herein certain new and novel methods of, and devices for, monitoring oxygen concentration in gaseous mixtures. These novel devices differ from the majority of the oxygen monitors described above in that they are compact, lightweight, and otherwise suited for on-airway mainstream monitoring of the oxygen concentration in a person's respiratory gases. The methods and monitoring devices disclosed herein utilize the fast (or breath-by-breath) approach to oxygen concentration monitoring with the quenching of a luminescent dye being used in determining the concentration of oxygen in the gases being monitored.

Fast (breath-by-breath) monitoring of end tidal oxygen is an important diagnostic tool because, as examples only:

1. It is a sensitive indicator of hypoventilation.
2. It aids in rapid diagnosis of anesthetic/ventilation mishaps such as (a) inappropriate gas concentration, (b) apnea, and (c) breathing apparatus disconnects.
3. End tidal oxygen analysis reflects arterial oxygen concentration.
4. Inspired-expired oxygen concentration differences reflect adequacy of alveolar ventilation. This is useful for patients undergoing ECMO (Extracaporeal Membrane Oxygenation) or nitric oxide therapies.
5. When combined with a volume flow device (e.g. a pneumotach), $VO_2$ (oxygen consumption) can be determined. Oxygen consumption is a very useful parameter in determining (a) oxygen uptake during ventilation or exercise, (b) respiratory exchange ratio or RQ (respiratory quotient) and (c) general patient metabolic status.

The novel sensor devices of the present invention locate a luminescent chemical in the patient airway. Modulated visible light excites the chemical and causes it to luminesce. The lifetime of the luminescence is proportional to the amount of oxygen present. A transducer containing a photodetector and associated electronic circuitry measures decay time and relates the measured parameter to the ambient oxygen partial pressure.

The transducer device is small (<1 cubic inch), lightweight (less than 1 ounce), and does not contain moving parts. It utilizes visible light optoelectronics and consumes minimal power (system power less than 2 watts). The unit warms up in less than 30 seconds, which is advantageous in on-airway applications because of the need to take prompt remedial action if a change occurs in a patient's condition reflected in a change in respiratory oxygen concentration. The assembly does not require any significant optical alignment and is very rugged (capable of being dropped from 6 feet without affecting optical alignment or otherwise damaging the device).

Yet another important advantage of the present invention is that its principles can be employed to advantage in sidestream (sampling) type systems as well as in mainstream systems. This is important because some gas analysis systems, such as anesthetic analyzers, employ sidestream techniques to acquire the gas sample.

A typical transducer unit is easy to calibrate, stable (±2 torr over 8 hours at a 21percent oxygen concentration), and has a high resolution (0.1 torr) and a wide measurement range (oxygen concentrations of 0 to 100 percent). Response to changing oxygen concentrations is fast (<100 ms for oxygen concentrations of 10–90 percent at flow rates ≈1l/min). The transducer is not susceptible to interference from anesthetic agents, water vapor, nitrous oxide, carbon dioxide, or other gases and vapors apt to be present in the environment in which the system is used.

The sensor comprises a polymeric membrane in which a luminescable composition such as a porphyrin dye is dispersed. The sensor membrane is the mediator that brings about dye-oxygen interaction in a controlled fashion. In a functional sensor, the dye is dispersed in the polymeric membrane, and oxygen diffuses through the polymer. The characteristics of the sensor are dependent upon the dye-polymer interaction and permeability and the solubility of oxygen in the polymer. Such characteristics include the sensitivity of response of the sensor to oxygen, the response time of the sensor to a change in oxygen concentration, and the measured values of phosphorescence intensity and decay time. Thus the composition and molecular weight of the polymer determines the sensor characteristics. Also, if the sensor is prepared by evaporation of a solution as described below, the film characteristics depend on the solvent that is used and conditions during casting or evaporation. If the dye is separately doped into the film from another solution, the solvent and conditions in the doping medium also affect the sensor characteristics. When the polymer film is prepared by polymerization of a monomer or mixture, the sensor characteristics depend on the conditions of polymerization and such resultant polymer characteristics as degree of crosslinking and molecular weight.

The luminescent chemical sensor is not toxic to the patient and is a part of a consumable (i.e., disposable) airway adapter weighing less than 0.5 ounce. The sensor shelf life is greater than one year and the operational life exceeds 100 hours. The cost of the consumable airway adapter is minimal.

It is also important that the oxygen monitoring system of the present invention has sufficient accuracy (1.0%), precision (0.01%), and response time (<100 ms) to monitor breath-by-breath oxygen concentrations. A related and important advantage of the present invention is that the sensor is not sensitive to other gases found in the airway, including anesthetic agents, and is accordingly not excited into luminescence by those gases. The sensitivity of the sensor to temperature, flow rate, pressure and humidity change is well understood; and algorithms which provide compensation for any errors due to these changes are incorporated in the signal processing circuits of the device.

It is a further advantage that the sensor can be easily (and even automatically) calibrated to single point room air oxygen, which is important because of the lack of availability of calibration gases in certain settings. The device is so stable that recalibration is not required for at least eight hours.

One embodiment of the present invention employs a single light source for exciting the luminescable composition of the sensor, a data detector on which light propagated from the luminescing composition falls as that luminescence is quenched by oxygen in the gases being monitored, and a reference detector for calibrating the data detector.

A second embodiment of the present invention employs two sources of light for exciting the sensor into luminescence and a single (data) photodetector. This arrangement has the advantage of eliminating measurement errors attributable to differential drift between the data and reference signal processing circuits.

Preferred embodiments of the visible light oxygen measurement transducers disclosed herein employ a novel sensor heater arrangement and a proportional-integrated-differential (PID) heater control system for keeping the oxygen concentration sensor of the transducer precisely at a selected operating temperature. This is particularly significant because the oxygen measurement transducers disclosed herein employ a sensor which involves the use of the diffusion of oxygen into a luminescable layer in measuring oxygen concentration. The rate of diffusion is temperature dependent. As a consequence, the measurement of oxygen concentration becomes inaccurate unless the sensor temperature is kept constant.

In on-airway applications of the invention, the oxygen concentration sensor takes the form of a thin film mounted in an airway adapter casing; and the sensor heater includes a highly conductive thermal capacitor for heating the sensor film. A novel assembly method insures that the sensor film is stretched over the thermal capacitor in the assembled airway adapter and that the thermal capacitor and sensor film are therefore in intimate physical contact. This further promotes the precision with which the sensor can be maintained at the selected temperature by guaranteeing a rapid transfer of heat between the thermal capacitor and the film so that the film temperature cannot drift to any appreciable extent from the selected operating temperature. This is reflected in an accurate oxygen concentration measurement.

In on-airway applications of the invention, the thermal capacitor in the airway adapter is heated by way of a floating, thermally conductive heater component in the oxygen measurement transducer to which the airway adapter is removably assembled. The floating heater and thermal capacitor are so configured that the heater snaps into firm physical contact with the capacitor as the airway adapter is assembled to the transducer. This insures that there is intimate contact between, and an efficient transfer of heat from, the floating heater to the thermal capacitor.

A thick film resistance heater can be used to heat the transducer's floating heater element. This element is preferably located on that side of the floating heater opposite the side contacted by the airway adapter thermal capacitor along with a temperature sensing component of the heater control system. The temperature sensor is incorporated in the PID control system for the thick film heater.

The location of the oxygen concentration sensor in a replaceable, simple component is an important feature of the present invention. This makes it possible to readily and inexpensively ensure that the system is sterile with respect to each patient being monitored by replacing the airway adapter between patients, avoiding the non-desireability (and perhaps the inability) to sterilize that system component.

The provision of an airway adapter sensor and a separate signal-producing transducer also has the practical advantage that a measurement of oxygen concentration can be made without interrupting either the ventilation of a patient, or any other procedure involving the use of the airway circuit. This is affected by installing the airway adapter in the airway circuit. When the time comes to make oxygen measurements, all that is required is the transducer be coupled to the airway adapter already in place. The adapter includes a casing made from a thermally non-conductive polymer that defines a passage through which the gases to be analyzed flow. The airway adapter sensor is coupled to a transducer to generate a signal indicative of the oxygen concentration in the gases flowing through the airway adapter. Another important feature of the invention insures that the airway adapter and transducer are assembled in the correct orientation and that the airway adapter and transducer are securely assembled until deliberately separated by the system user.

The signals generated by the novel oxygen-measurement transducers disclosed herein must be processed to remove noise and extract the luminescence decay time, which is the oxygen-sensitive parameter of interest. A lock-in amplifier is preferably employed for this purpose. The lock-in amplifier outputs a signal which has a phase angle corresponding to the decay time of the excited, luminescent composition in the oxygen concentration sensor. The lock-in detection circuitry rejects noise and those components of the photodetector-generated signal which are not indicative of oxygen concentration. This noise reduction also allows a higher level of signal gain which, in turn, makes possible enhanced measurement precision while decreasing the level of the visible excitation. This reduces instability from photo aging of the sensor, increasing accuracy and useable life. All of this processing, which can be done with digital, analog, or hybrid methods, is fast enough for even the most demanding applications such as those requiring the breath-by-breath monitoring of a human patient. Various pathological conditions result in a change of oxygen demand by the body. If a decrease of oxygen utilization by the body, for example, can be detected on a breath-by-breath basis, timely and effective remedial steps can be taken to assist the patient.

In the novel oxygen measurement transducers of the present invention, the concentration of oxygen in the gases being monitored is reflected in the quenching of an excited luminescent composition in the oxygen concentration sensor by oxygen diffusing into the sensor matrix. A source consisting of a light-emitting diode (LED) produces visible exciting light which strikes the surface of the sensor film. Some of the light is absorbed by the luminescent chemical dye in the film whereupon it produces luminescent light at a second, shifted wavelength. All light directed toward the photodetector can potentially result in a signal. A suitable optical filter placed over the surface of the photodetector discriminates against all but the luminescent light, thereby ensuring that the photodetector is producing a signal related to oxygen concentration only. The goal of isolating the photodetector from light which is not indicative of oxygen concentration can be furthered by a geometric relationship of the light source and photodetector as established by the configuration of an optical platform on which the light source and photodetector are mounted. This geometric relationship places the photodetector at a location away from the specular reflection of the LED light off of the surface, further optimizing the ratio of luminescent light to other, stray or reflected light that might reach the detector.

The novel oxygen-sensitive sensors employed in the present invention include a luminescent composition, uniformly distributed over and embedded in a thin, porous polymer matrix, a scheme which ensures a fast sensor response time. Novel methods, disclosed herein, for manufacturing these sensors are simpler than those heretofore proposed, give more reproducible results, and allow the matrix to be fabricated from a wide variety of polymers with desirable characteristics. In these methods, a solution of the selected luminescent dye is painted onto, or soaked into, a porous polymeric membrane or sandwiched between two membranes of the selected polymer. Due to the porous structure of the starting polymers, the films or membranes have the advantage that the molecules are embedded within microns of the gas-polymer interface and have fast response times. As the starting material is a thin polymeric membrane, batch processing of films of uniform composition and characteristics is facilitated.

As suggested above, on-airway monitoring is a particularly advantageous application of the present invention. The principles of the present invention can, nevertheless, be advantageously employed in other gas monitoring techniques; notably, sidestream sampling, and can be used to monitor the oxygen concentration of other than respiratory gases.

The objects, features, and advantages of the invention will be apparent to the reader from the forgoing discussion and the appended claims and as the ensuing detailed description of the invention proceeds in conjunction with the accompanying drawings.

DESCRIPTION OF THE DRAWINGS

FIG. 3 is an exploded view which includes a perspective of the transducer and illustrates how the airway adapter is kept from being incorrectly assembled to the transducer;

FIG. 4 is an exploded view of the transducer showing the two components of the transducer casing and an assembly which includes the optical components of the transducer and a platform to which those components are mounted;

FIG. 5 is a transverse section through the airway adapter taken primarily to show the details of the oxygen sensor incorporated in the airway adapter and of a thermal capacitor included in the airway adapter to keep the temperature of the oxygen sensor constant;

FIG. 6 is a longitudinal section through the airway adapter and is provided to show: the passage through the adapter for the gases being monitored, the oxygen concentration sensor and thermal capacitor, and a window which transmits light to and from the oxygen sensor;

DETAILED DESCRIPTION OF THE INVENTION

Figure 1:
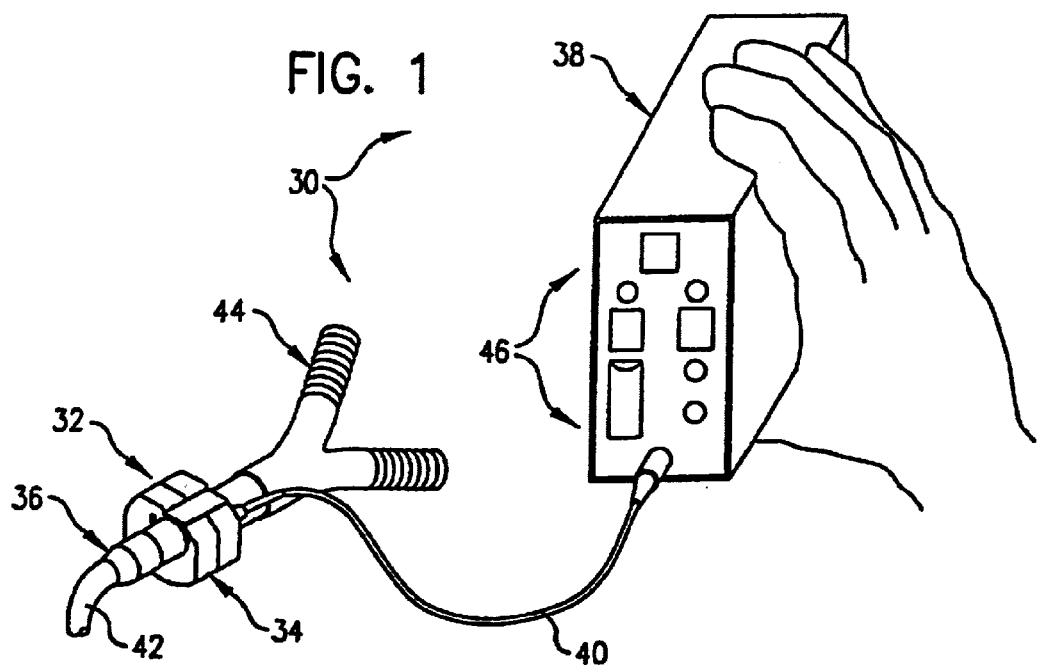
FIG. 1 is a generally pictorial view of an on-line system for monitoring the oxygen concentration in a patient's breath; the system is constructed in accordance with and embodies the principles of the present invention.

Referring now to the drawings, FIG. 1 depicts oxygen concentration monitoring apparatus 30, which is constructed in accordance with and embodies the principles of the present invention. The major components of apparatus 30 include an on-line assembly 32 of a transducer 34 and an airway adapter 36. The particular apparatus 30 illustrated in FIG. 1, also includes a hand held control and display unit 38 which is connected to transducer 34 by a conventional electrical cable 40.

In the particular application of the present invention illustrated in the drawings, apparatus 30 is employed to monitor the concentration of oxygen in a patient's respiratory gases. To this end, airway adapter 36 is connected in line between an endotracheal tube 42 inserted in the patient's trachea and the plumbing or breathing circuit 44 of a mechanical ventilator (not shown).

Airway adapter 36 and transducer 34 cooperate to produce an electrical signal indicative of the oxygen concentration in the gases flowing from endotracheal tube 42 through airway adapter 36 to plumbing 44. This signal is transmitted to unit 38 through cable 40 and converted to a numerical designation, which appears on the display array 46 of unit 38.

The just-described two-component system meets the requirement that monitoring be accomplished without interrupting the flow of gases through breathing circuit 44 or other patient connected flow circuit. Transducer 34 can be removed, for example, to facilitate or enable the movement of a patient, leaving airway adapter 36 in place to continue the vital flow of gases.

Apparatus 30 also has, in this regard, the advantage that there are no electrical components in the airway adapter 36. Hence, there are no potentially dangerous electrical connections to the airway adapter or exposure of a patient to electrical shock.

Figure 2:
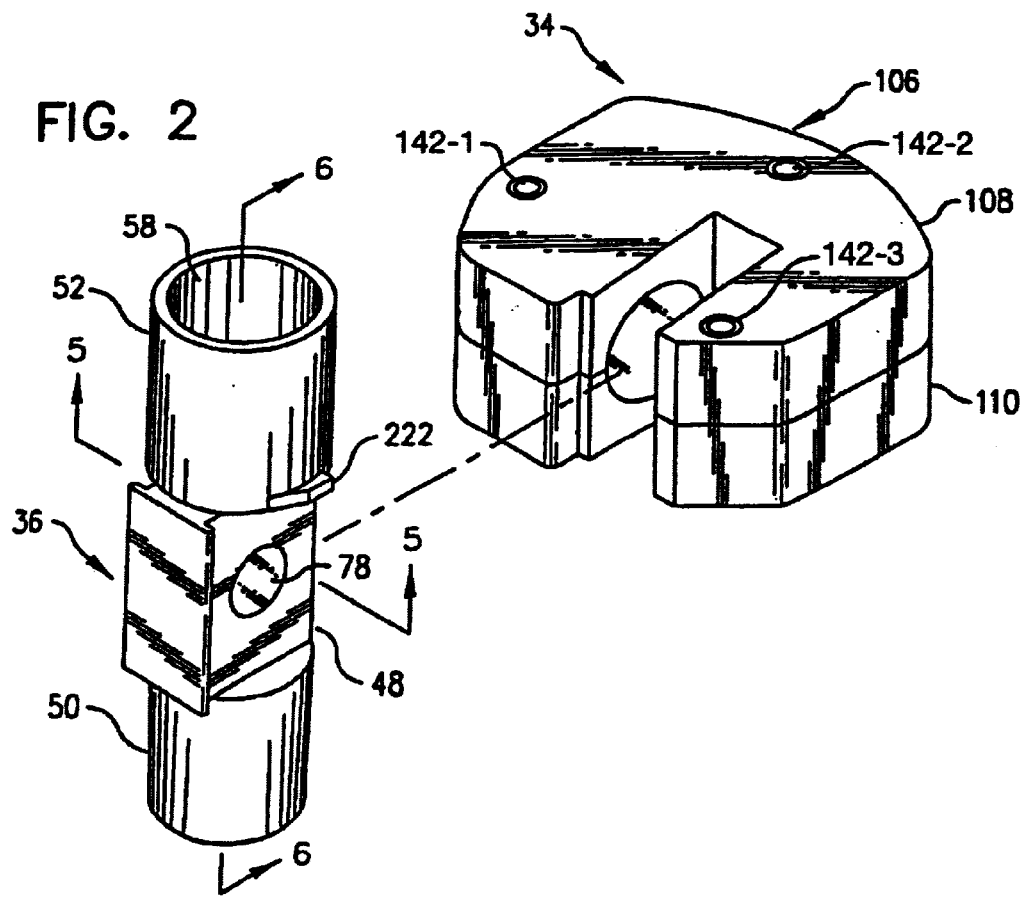
FIG. 2 is an exploded view of an airway adapter and a complementary transducer employed in the FIG. 1 system; the airway adapter has a sensor for oxygen in respiratory gases flowing through the adapter and the transducer acts with the airway adapter to provide a signal indicative of the concentration of the oxygen in the monitored gases.
Figure 7:
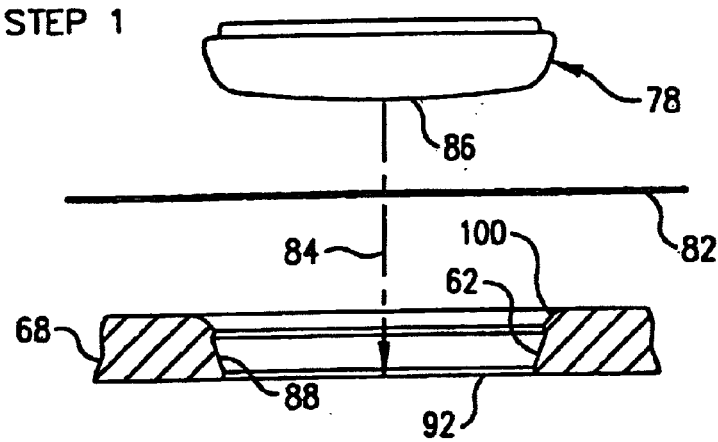
FIGS. 7–10 show the steps employed in installing the oxygen concentration sensor and the thermal capacitor in the casing of the airway adapter.
Figure 8:
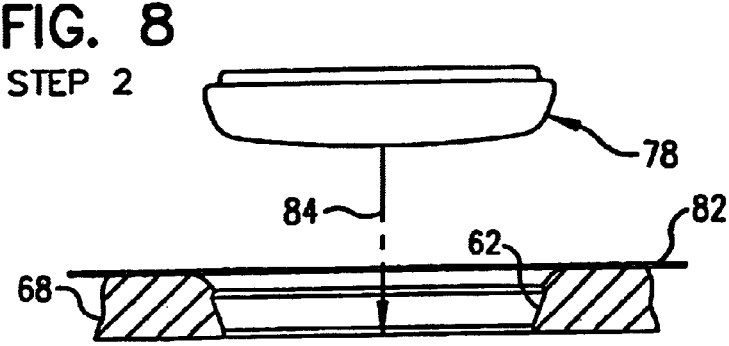
Figure 9:
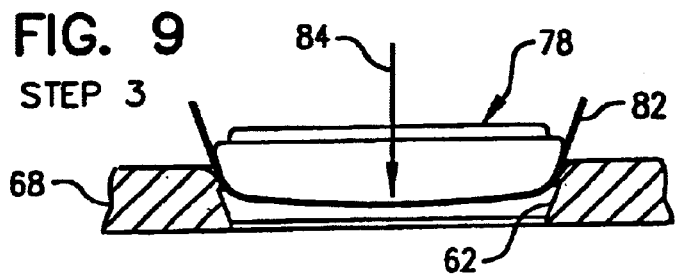

Referring now most specifically to FIGS. 2, 3, and 6, the exemplary, illustrated airway adapter 36 is a one-piece unit typically molded from VALOX® polycarbonate or a comparable polymer which is rugged and can be molded to close tolerances. An opaque material is employed to keep ambient light from reaching a light sensitive sensor component 47 (FIG. 5) of the airway adapter 36 through the walls of the airway adapter 36. Such extraneous light would adversely affect the accuracy of the oxygen concentration reading which the apparatus is designed to provide.

Airway adapter 36 has a generally parallelepipedal center section 48 and hollow, cylindrical end sections 50 and 52, each of which are also referred to herein collectively as airway adapter elements. Axially aligned passages 54, 56, and 58, respectively found in airway adapter elements 50, 48, and 52, define a flow passage 60 extending from end-to-end through airway adapter 36.

As shown in FIGS. 2 and 6, end section 50 of airway adapter 36 is configured as a male connector, and end section 52 is configured as a female connector. This allows the airway adapter 36 to be connected into conventional anesthetic and respiratory circuits.

As is perhaps best shown in FIGS. 5 and 6, apertures 62 and 64 aligned along transverse axis 66 are formed in opposed side walls 68 and 70 of airway adapter central element 48. An oxygen concentration sensor assembly 72 is mounted in aperture 62, and a window 74 is mounted in aperture 64 facing sensor assembly 72 and on the opposite side of the sensor component 47 from flow passage 60.

Figure 10:
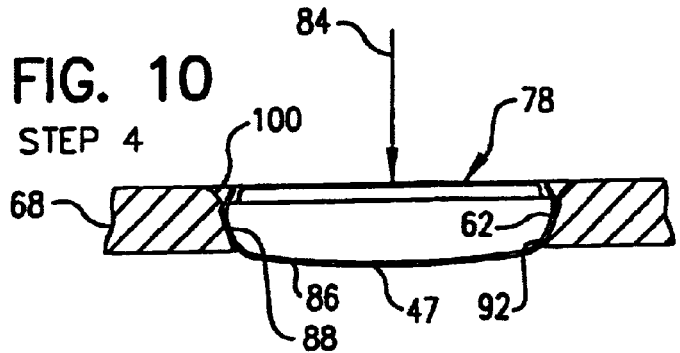
Figure 11:
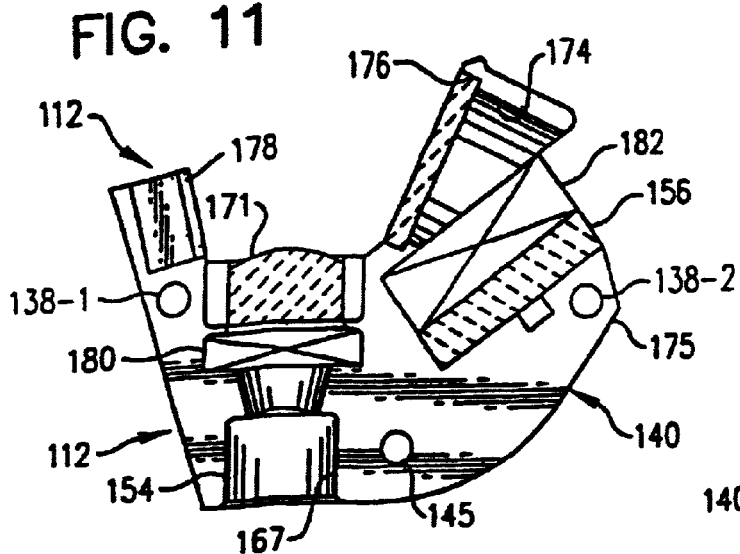
FIG. 11 is a cross-sectional plan of the optical platform subassembly of the transducer; the optical components of the transducer are mounted to the platform of this subassembly.
Figure 12:
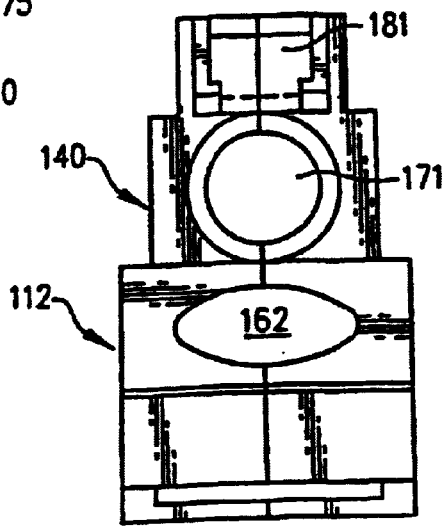
FIG. 12 is a front view of the optical platform subassembly.

Sensor assembly 72 (see FIGS. 5, 6, and 10) is composed of sensor 47 and a thermal capacitor 78. Sensor 47 is a thin film which is stretched over and thereby in intimate contact with the thermal capacitor 78. As will be discussed later, thermal capacitor 78 is employed to maintain sensor component 47 at a constant operating temperature and thereby eliminate inaccuracies in oxygen concentration measurement attributable to variations in the temperature of sensor component 47.

Sensor component 47 is made up of a thin, microporous, hydrophobic polymeric matrix with a luminescable composition disposed in the matrix. The preferred luminescable compositions are photostable, phosphorescent dyes, which absorb energy having a frequency between 300–700 nm, emit energy with a frequency in the range of 500–1000 nm, and have a luminescence decay time in the range of 1–1000 microseconds.

Oxygen monitoring apparatus embodying the principles of the present invention operates on the principle that the luminescable composition of sensor component 47 can be excited into luminescence by a pulse of light of an appropriate frequency with that light being absorbed by the luminescable composition and re-emitted at a shifted wavelength over, typically, a period measured in microseconds. Oxygen in gases passing through the flow passage 60 of airway adapter 36 quenches the luminescing composition. The quenching of the composition is related to the oxygen concentration of the gases flowing through airway adapter flow passage 60. As the oxygen concentration increases, the quenching of the excited state of the composition does likewise; and the intensity and characteristic decay time of the luminescence decreases. This quenching is a dynamic process with response of the sensor to a change in oxygen concentration being sufficiently fast to allow monitoring of oxygen on a breath-by-breath basis. No chemical reactions occur in the excitation/quenching cycle, so the luminescable composition is not used up in the oxygen monitoring process.

Previous attempts to employ luminescence quenching in the measurement of oxygen concentration have focused on increasing illumination of the oxygen sensor, thereby increasing the magnitude of response of the sensor to changes in the oxygen concentration of the gases being monitored. However, the high illumination level gives rise to rapid photo aging of the sensor film, limiting accuracy and stability. Systems employing the principles of the present invention, in contrast, decrease the illumination level and use higher electronic gain of the detector generated electrical signal, and selective noise reduction, reducing the instability due to photo aging of the sensor film to acceptable levels.

A large-area photodiode detector further facilitates the use of decreased illumination levels. The size of the LED beam can also be expanded to fill a larger area of the sensor film, thereby lowering the intensity of illumination per unit area while leaving the total signal nearly unchanged. This, along with slight aperturing of the LED beam and reduction of the LED duty cycle (pulse rate), easily leads to an order-of-magnitude decrease in aging rate.

The presently preferred luminescable compositions are porphyrins. Porphyrins are stable organic ring structures that often include a metal atom. When the metal atom is platinum or palladium, the phosphorescence decay time ranges from 10 microseconds to 1000 microseconds. This gives a high sensitivity to oxygen and allows fairly simple electronic detection of the energy emitted by the excited composition.

Some of the synthetic porphryins are especially stable with respect to photodegradation. The fluorinated porphyrins; e.g., the meso-tetraphenyl porphines, are especially photostable. Luminescable compositions of this character which can be employed to advantage in systems employing the principles of the present invention are: platinum meso-tetra (pentafluoro) phenyl porphine, palladium meso-tetra (pentafluro) phenyl porphine, platinum meso-tetraphenyl prophine, and palladium meso-tetra phenyl prophine.

The sensor membrane (or matrix) is an important element of apparatus embodying the principles of the present invention because it brings about sensor composition-oxygen interaction in a controlled fashion. The luminescable compositions are dispersed in the polymer as by evaporation, doping, or in situ polymerization. The characteristics of the sensor are dependent upon the composition-polymer interaction and the permeability and solubility of oxygen in the polymeric matrix. Such characteristics include the sensitivity of the sensor to oxygen, the response time of the sensor to a change in oxygen concentration, and the measured values of phosphorescence (a luminescence) intensity and decay time.

The composition and molecular weight of the polymer also determine the sensor characteristics. Furthermore, if the polymer film is prepared by evaporation of a solution, the film characteristics depend on the solvent and the process conditions during casting or evaporation. If the luminescable composition is separately doped into the film, the solvent and process conditions employed in the doping also affect the sensor characteristics. When the polymer film is prepared by polymerization of a monomer or mixture, the sensor characteristics depend on the conditions of polymerization and such resultant polymer characteristics as degree of crosslinking and molecular weight.

In short, a variety of nonobvious factors must be taken into account in selecting the membrane material and in fabricating the membrane from the selected material.

The aforementioned process parameters enable a high degree of engineering of sensor characteristics. At the same time, many variables are controlled, resulting in the production of sensor films of optimized, uniform characteristics.

Many previous approaches to phosphorescence quenching have focused on silicone polymers due to their high oxygen permeability. These polymers, however, suffer from low solubility for many phosphorescent organic or organometallic compounds and low signals resulting from the low luminescable composition content and high quenching although the high oxygen diffusion rates in silicone films gives a rise to short response time to changing oxygen concentration (e.g., less than 1 sec.), which is desirable.

Other types of polymers yield films with large signals but long response times (e.g., many seconds). In respiratory oxygen measurements, very short response times (ca. 100 milliseconds) are desirable. Consequently, films made from polymers with the characteristics just discussed are less than satisfactory or even completely unusable.

Nevertheless, there are polymers from which membranes (or matrices) that are suitable for sensors as disclosed herein can be made. These include porous polyvinyl chloride, polypropylene, polycarbonate, polyester, polystyrene, and polymethylacrylate polymers and acrylic copolymers. Those materials resemble thin sections of porous sponge with a high volume fraction of air space. They are ideal for introducing a solution which can be absorbed into the polymer, yielding an altered membrane with the luminescable composition molecularly dispersed in the polymeric matrix.

Representative of the polymers identified above which are usable for sensors embodying the principles of the present invention are microporous polycarbonates marketed by Gelman-Sciences, Whitman, and Osmonic/Poretics. Currently preferred are the track-etched, microporous filtration membranes of Osmonic/Poretics. Track-etched polymers have the advantage in the context of the present invention that the particles of luminescable composition are readily captured on the surface of the sensor matrix.

Irrespective of the polymer which is selected, it is preferred that the sensor film or membrane have a thickness of 5 to 20 $\mu$m and a pore size ranging 0.1 to 10 $\mu$m as the diffusion constant for oxygen in films of those parameters is large enough to provide a response time of sufficiently short duration.

The Osmonics/Poretics track-etched polycarbonate with a 0.4 $\mu$m pore size and a thickness of 10 $\mu$m is the preferred membrane material. This material has many advantages. Its thin porous structure facilitates incorporation of the luminescable composition into the polymeric matrix, such that all of the composition in the matrix is only a short distance from the gases being monitored. This allows oxygen in those gases to rapidly diffuse into the matrix and into contact with the luminescable composition. Fast diffusion translates into a fast response to the oxygen in the gases being monitored.

The uniform polymeric structure of the Osmonics/Poretics material gives rise to easily manufactured matrices with the same, reproducible characteristics. This polycarbonate film has excellent signal response (i.e., change of signal with change in oxygen). Also, these films seem to show a higher degree of photostability (i.e., less change or photo aging over a given time of luminescence).

As indicated above, a number of techniques can be employed in accordance with the principles of the present invention to disperse the luminescable composition in the polymeric matrix.

The composition may be dissolved in an appropriate solvent which is capable of swelling the polymeric material, thereby allowing the luminescable composition to be readily introduced into the matrix. The solvent interacts strongly with the polymer material, but the interaction is not so great as to cause the polymer to dissolve in the solvent. Since this solvent has the luminescable composition dissolved in it, the swelling of the polymer by the solvent carries the composition into the polymer matrix. The impregnated matrix is then dried to evaporate the solvent. When the solvent evaporates, the luminescable composition is left behind, incorporated in and molecularly distributed within the polymer matrix.

Others have attempted to disperse a luminescable composition in a polymeric matrix by dissolving the composition in a mixture containing the monomer or polymer precursors and then initiating a polymerization reaction. The methods disclosed herein and utilizing swelling of the polymer to introduce the luminescable composition into the sensor matrix have the advantage of being simpler and more reproducible and of allowing the use of virtually any polymer which does not appreciably dissolve when the solvent is applied.

A variety of solvents are suitable. These include hexane, petroleum ethane, toluene, tetrahydrofuran, methylene chloride, trichloroethylene, xylene, dioxane, isopropyl alcohol, butanol and mixtures including those solvents with the particular solvent depending upon the polymer and luminescable composition that are employed.

The solution of luminescable composition in swelling solvent may be painted onto the polymeric membrane. The polymeric matrix can, in an alternate approach in accordance with the principles of the invention, be soaked in the solution of luminescable composition and swelling solvent.

In the approaches just described, the solvent is removed by drying the membrane in air or by gas, leaving the luminescable composition dispersed and trapped in the polymeric matrix.

In yet another sensor fabrication technique embodying the principles of the present invention, the swelling solvent-luminescable composition solution is sandwiched between two thin polymeric membranes such that the two membranes become solvent bonded together. This can be accomplished either by using an attacking solvent in the solution or by further application of an attacking solvent or solvent mixture to the top membrane.

In this process of fabricating an oxygen sensitive sensor, the luminescable composition is effectively introduced into the center of the resulting polymer film and, when the two polymer layers are fused together, the sandwiched luminescable composition is incorporated in the structure of the polymer. The attacking solvents must dissolve both the composition and the polymer to some extent so the composition can be carried into the polymer matrix. Since the luminescable composition penetrates from the center of the resulting film, this is a way to incorporate a greater quantity of luminescable composition into a film to have a higher concentration of luminescable composition in the center of the thin dimension of the film, where it is less exposed and more protected.

Due to the thin, porous structure of the starting polymers, sensor films embodying the principle of the present invention have the advantage that the molecules of the luminescable composition are embedded within microns of the gas-polymer interface and have fast response times. The pores serve as channels for introducing the composition into the porous polymeric matrix, allowing a three-dimensional incorporation of the diffusing composition. Where the solvents do not strongly attack the polymer structure, the pores survive and gas diffusion into the polymer membrane is enhanced due to the short diffusion distances. Since the starting material is a thin polymer with a high degree of manufactured uniformity, batch processing of sensors of uniform composition and characteristics is facilitated.

Irrespective of the process that is selected, the characteristics of the sensor can be modified, if advantageous, by overcoating the impregnated polymeric matrix with an additional polymeric film. This can be accomplished by painting a dilute solution of the polymer in a volatile solvent on the matrix or by solvent bonding an additional thin polymeric membrane on the surface of the film.

Overcoating is used to refine the characteristics of the film. The primary characteristics of the luminescence result from the particular luminescable composition and the particular polymer in which it is dissolved. Characteristics of the overall sensor that may be modified by overcoating the matrix polymer include light absorption and transmission properties, gas permeability, and interaction with solvents or other chemical substances. For example, if a sensor film consisting of a dye in a given polymer has nearly ideal characteristics, but it is desired to decrease the level of diffusion of oxygen into the film, this may be accomplished by overcoating the film with a thin layer of a polymer which is less oxygen permeable than the matrix material. The desirable properties of the original film are retained but have a less sharp response to oxygen, more signal, and less quenching. The overall effect is to provide the matrix film with characteristics that can not be obtained by simply dissolving the luminescable composition in existing material.

The following example presents one representative method for making an oxygen sensor embodying the principles of the present invention.

EXAMPLE

A 10 μm thick Poretics® track-etched polycarbonate with a 0.4 micron pore size supplied by Osmonics/Poretics, Livermore, CA, is used as the polymeric matrix of a sensor. A mixed solvent is prepared by mixing 3 ml of methylene chloride (Mallinckrodt, UltinitAR®) with 7 ml of toluene (Mallinckrodt, AR®). To 10 ml of this mixed solvent is added 15 mg of platinum meso-tetra (pentafluorophenyl) porphine (Pt TFPP, Porphyrin Products, Logan Utah). Slight stirring of the mixture gives complete dissolution of the porphyrin, resulting in a red-orange dye solution.

One-inch disks or one-inch squares of the polycarbonate film are placed separately in the bottom of a small glass beaker or on top of a glass plate, and the dye solution is added dropwise to the film pieces until they are saturated with solution. Over several minutes, a gentle buckling and swelling of the film is evident, after which several drops of dye solution are added to each film segment.

As the solvent begins to evaporate, the film pieces are transferred to other glass slides with forceps clipped to a small wooden stirring stick or a wire and hung over the top of a small, empty beaker. Excess remaining solution is then washed from the film surface by transferring isopropyl alcohol from a pipette to the top of the hanging film and allowing the alcohol to drip off the bottom surface. Afterwards, each film piece is dried and cut to size for mounting in airway adapters 36 as shown in FIG. 6 of the drawings.

Turning now to FIGS. 7–10 of the drawings, an important feature of the present invention is a novel process for installing sensor component 47 in an aperture 62 which is formed in the wall 68 of airway adapter center section 48. A sensor blank 82 is placed between thermal capacitor 78 and airway adapter side wall 68 (Step 1, FIG. 7) and then lowered (Step 2, FIG. 8) until the blank 82 rests on side wall 68 in overlying relationship to aperture 62 (Step 3, FIG. 9). Then, thermal capacitor 78 is displaced in the direction indicated by arrow 84, pushing the sensor blank 82 toward the aperture 62 of airway adapter 36 center section 48 (not shown) as thermal capacitor 78 moves into aperture 62 (Step 4, FIG. 10). Friction between the domed side 86 of the thermal capacitor 78 and sensor blank 82 and between sensor the blank 82 and the periphery 88 of airway adapter aperture 62 causes blank 82 to be stretched over the domed side 86 of the thermal capacitor 78 as that airway adapter component moves to the installed position of FIG. 10. This tightens the blank against thermal capacitor domed side 86 and provides firm, intimate contact between the sensor and the thermal capacitor. This is important because the energy outputted by sensor component 47 when it is excited into luminescence is very temperature dependent. With intimate contact between the sensor component 47 and thermal capacitor 78, temperature variations of sensor component 47 during the operation of apparatus 30 can be reduced to an acceptable minimum, if not entirely eliminated, by controlling the temperature of the thermal capacitor 78 with an important and novel way of accomplishing this objective being discussed hereinafter.

A circumferential lip 92 is provided at the inner end of aperture 62 in airway adapter center section 48. This lip stops the sensor assembly 72 of thermal capacitor 78 and sensor component 47 at the proper location relative to the boundary of the aperture 62 through airway adapter center section 48. A second circumferential lip 100 at a location intermediate the inner and outer ends of aperture 62 holds sensor assembly 72 in place in the designated position and keeps the sensor assembly 72 from popping out of the airway adapter side wall 68.

Referring now primarily to FIGS. 1–4 and 11–13 of the drawings, transducer 34 is employed to excite sensor component 47 into luminescence and to convert the light emitted by the excited sensor component 47 to an electrical signal indicative of the oxygen concentration in the gases flowing through airway adapter passage 60 (not shown). The transducer 34 includes a casing 106 composed of casing components 108 and 110. Housed in casing 106 are an optical subassembly 112, a sensor heater system 114, and a printed circuit board (PCB) 116.

Figure 13:
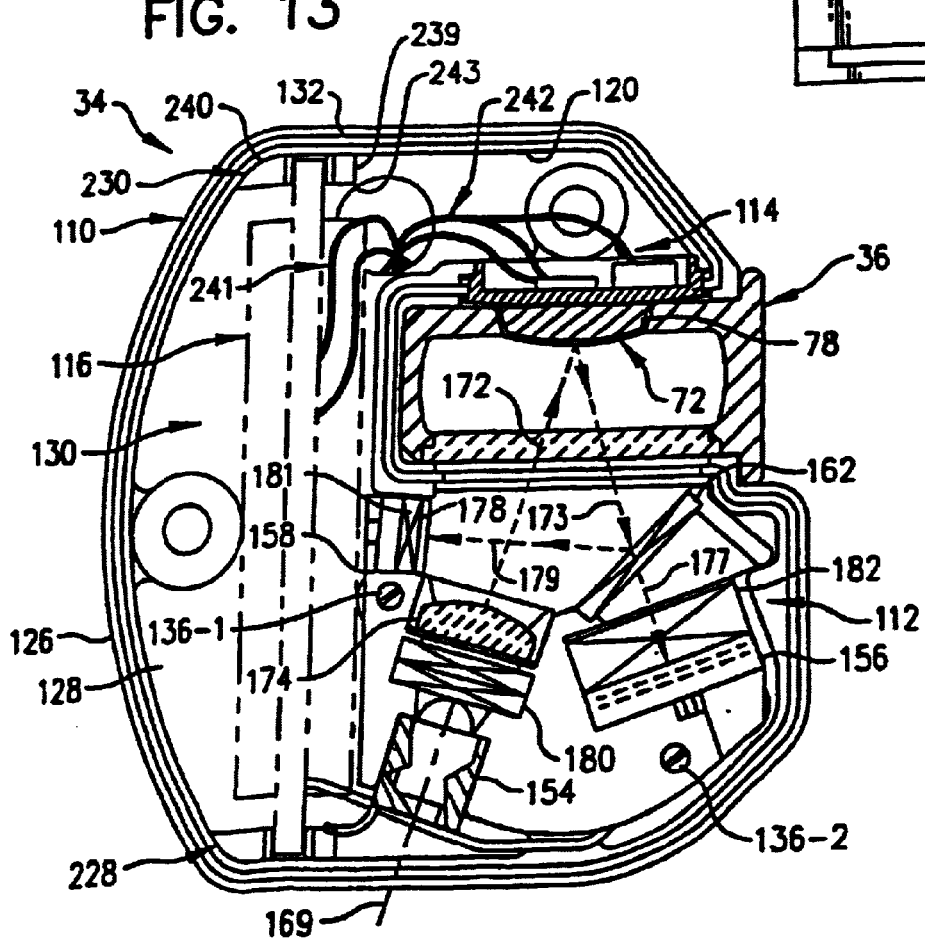
FIG. 13 is a view of the transducer with one of the two casing components removed and certain components sectioned to show the internal components of and the optical paths in the transducer.

More specifically, and as is shown in FIGS. 4 and 13, transducer casing components 108 and 110 have cavities 118 and 120 defined by the side and end walls 122 and 124, respectively, of casing component 108 and by the side and end walls 126 and 128, respectively, of casing component 110. These cavities cooperate to define an enclosed compartment (or well) 130 in which the just-enumerated components or subassemblies of transducer 34 are housed. A lip 132 on the side wall 126 of casing component 110 fits into a complementary recess 134 of side wall 122 to fix the two casing components 108 and 110 together and to provide a tongue and groove seal which keeps water and other foreign material from penetrating into casing compartment 130.

Optical assembly 112 is placed in casing component 110 and fastened in place by screws 136-1 and 136-2 which extend through apertures 138-1 and 138-2 (FIG. 11) of the platform 140 (FIG. 11) of the optical subassembly 112 into blind tapped apertures (not shown) in casing component 110. Casing component 108 is then placed over the optical subassembly 112 and fastened in place with three screws 142-1, 142-2, and 142-3 (FIG. 4). Screw 142-1 extends through boss 144 of casing component 108 (FIG. 4) and aperture 145 in platform 140 (FIG. 11) into blind, tapped aperture 146 in boss 147 of casing component 110 (FIG. 4). Screws 142-2 and 142-3 extend through apertured bosses in casing component 108 directly into blind, tapped apertures in bosses of casing component 110 (the casing component 108 boss and the complementary boss in casing component 110 for screw 142-3 are shown in FIG. 4 and identified by reference characters 148 and 150.)

Referring now primarily to FIGS. 1, 4 and 11–13, the optical subassembly 112 of transducer 34 includes the above-eluded-to platform 140, a light source 154, data and reference detectors 156 and 158, signal processing circuitry (shown in FIGS. 17, 18, and 20) and a beam splitter 162. Data detector 156 and reference detector 158 are conventional PIN photodiodes supplied by Centronic, Newbury Park, Calif., and beam splitter 162 may be as simple as a piece of clear glass or plastic.

Light source or LED 154 is mounted in a socket 167 formed in optical platform 140. Bright green and blue LEDs are essentially ideal light sources. These LEDs have high intensity in the needed luminescable composition absorption region with little non-useful output at other wavelengths, especially near ultraviolet. This minimizes stray interfering light and photodegradation of the sensor.

Other advantages of these LEDs are their light weight, compactness, low power consumption, low voltage requirements, low heat production, reliability, ruggedness, relatively low cost, and stability. Also they can be switched on and off very quickly, reliably, and reproducibly. A representative light source is a bright green LED supplied by Nichia Chemical Industries, Ltd. and modulated (i.e., turned on and off) at a frequency of 4 kHz.

LED 154 is oriented with its axis of propagation 169 (see FIG. 13) at a 45° angle to sensor component 47. The light emitted from light source 154 is refocused into a beam by a lens 171 also installed in platform 140. The beam is propagated along optical path 172 to excite the luminescable composition of sensor component 47 into luminescence. Oxygen in gases moving through the flow passage 60 in airway adapter 36 quenches the luminescence exhibited by sensor component 47 in a way which reflects the concentration of oxygen in those gases. The luminescable composition of excited sensor component 47 emits light in the red part of the electromagnetic spectrum.

The emitted energy is propagated along optical path 173 through beam splitter 162 to data detector 156. Beam splitter 162 is mounted in a recess 174 located in an inclined element 175 of optical platform 140 in-line with an opening 176 through that platform element.

Light of a wavelength which can be processed into a signal indicative of the concentration of oxygen in the gases flowing through airway adapter passage 60 is transmitted by beam splitter 162 through aperture 176 to data detector 156 as indicated by arrow 177. Light is also reflected by beam splitter 162 through filter 181 to reference detector 158 as indicated by arrow 179.

It is important, from the viewpoint of accuracy, that only electromagnetic energy containing oxygen concentration data reach data detector 156. This is accomplished in transducer 34 with filters and by establishing a particular geometric relationship between light source 154 and data detector 156. More specifically, a filter 180, green for a green LED and blue for a blue LED, is mounted on optical platform 152 (FIG. 14) between LED 154 and lens 171, and a red filter 182 is mounted to that optical platform 152 between beam splitter 162 and data detector 156. Red filter 182 screens from data detector 156 all but the red light indicative of the oxygen concentration in the gases flowing through airway adapter flow passage 60.

A very small fraction of the light emitted by LED 154 falls in the red part of the visible spectrum. LED filter 180 (green or blue) keeps this red light from reaching sensor component 47, thereby promoting the accuracy of the oxygen concentration as seen by the data detector 156.

A fraction of the light emitted by LED 154 is not absorbed by sensor component 47 but is reflected from the sensor along the path of arrow 177, for example. A small part of that light is reflected by beam splitter 162 in the direction of arrow 179 onto reference detector filter 181, passing through that filter to reference detector 158. Filter 181 will typically be green or blue, depending on the color of LED 154. The filter 181 consequently screens out any red light indicative of oxygen concentration reaching the reference detector 158. Consequently, the light reaching the reference detector 158 contains only data which is not indicative of oxygen concentration and can accordingly be used to correct changes due to the LED 154 or optical path as one example.

Figure 14:
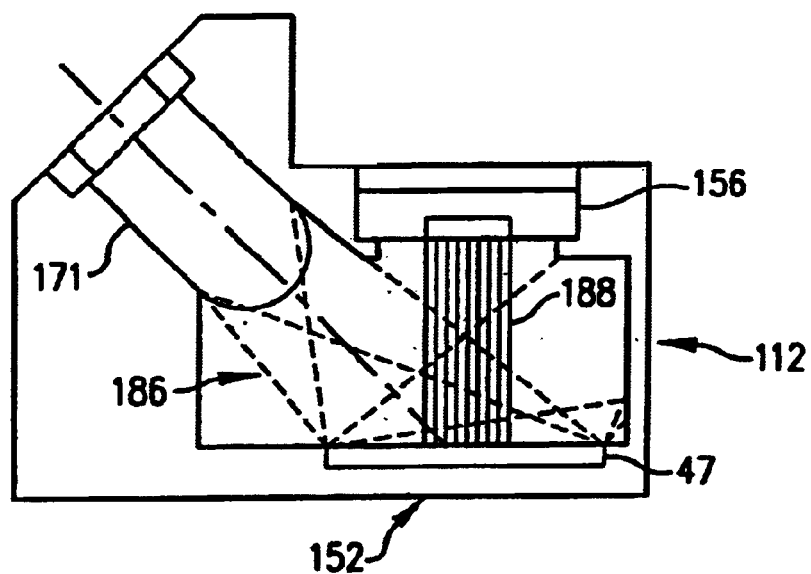
FIG. 14 is a generally pictorial view showing how a light source and a data detector in the transducer are so geometrically related by the platform of the optical subassembly that unwanted light which might affect the accuracy of the oxygen concentration signal outputted from the transducer is kept from reaching the detector.

Referring now most specifically to the pictorial representation of optical subassembly 112 in FIG. 14, a part of the light emitted by LED 154 is not absorbed by the luminescable composition in sensor component 47 but is instead reflected from this sensor as shown by the dotted lines collectively identified by reference character 186. This specular reflection is kept from data detector 156 and interfering with the accuracy of the oxygen-indicative signal produced by the data detector 156 by making the angle between LED 154 and data detector 156 such that reflected rays of light do not reach the data detector 156. Instead, only the light emitted by the luminescing composition, shown in solid lines 188 in FIG. 14, and carrying oxygen concentration information reaches data detector 156.

Referring now to FIGS. 5, 6, 13, 15, and 16, heretofore unaddressed is the necessity of maintaining the sensor of a luminescense quenching oxygen monitoring system at a constant temperature. This is necessary because as mentioned above, the emission of light from the luminescable composition in sensor component 47 is very temperature sensitive, because changing flow rates and the temperature of the gases being monitored significantly effect the temperature of the sensor component 47, and because the polymeric matrix of the sensor is by itself not capable of rapidly responding to temperature changes in the gases being monitored. In exemplary oxygen concentration monitoring apparatus 30, this problem is solved by: the use of thermal capacitor 78 in conjunction with the heating system components shown in FIGS. 13, 15, and 16, the aggressive heater control shown in FIG. 19 and identified by reference character 190, and with the above-described novel technique for so installing sensor component 47 in airway adapter end section 50 that the sensor is stretched tightly over, and remains in an intimate, heat transfer promoting relationship with, the thermal capacitor 78.

Sensor heating system 114 includes, in addition to thermal capacitor 78, a thermally conductive base 192, a thick film resistance heater 194, and a temperature sensor 196. Heating system conductive base 192 is installed in an aperture formed by complementary moon-shaped recesses 200 and 202 (see FIG. 4) in side walls 122 and 126 of transducer casing components 108 and 110. A lip 203 surrounding aperture 200/202 is trapped in a recess 204 which extends around the periphery of the installed heater system conductive base 192 to retain that heating system conductive base 192 in place.

Figure 15:
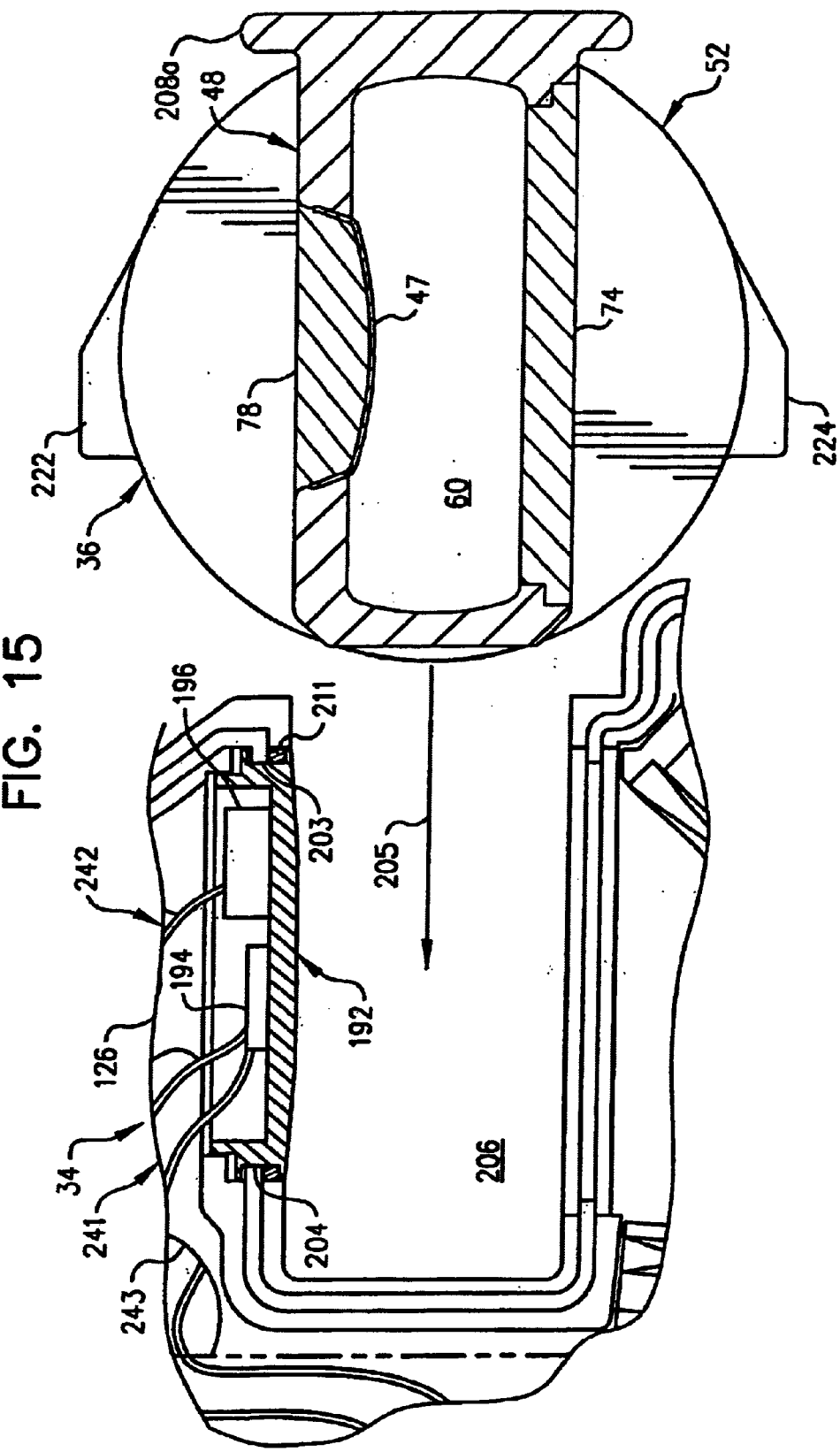
FIG. 15 is a fragmentary exploded view of the FIG. 2 system components showing how the airway adapter fits the transducer.
Figure 16:
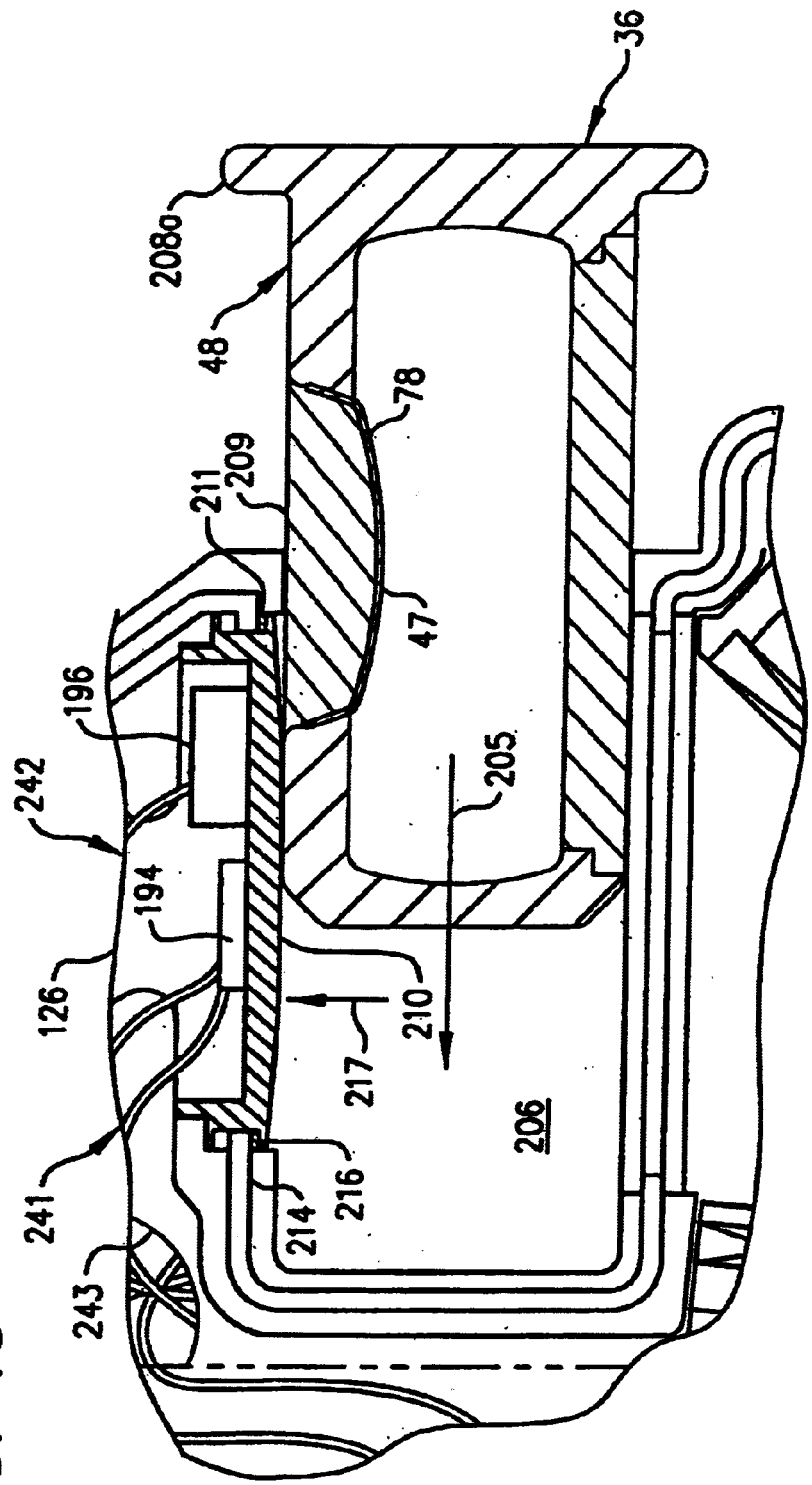
FIG. 16 is a view similar to FIG. 15 but showing the airway adapter partially installed in the transducer with the thermal capacitor in the airway adapter coming into conductive heat transfer relationship with a complementary heater in the transducer.

Referring now most specifically to FIGS. 13, 15 and 16, airway adapter 36 is removably assembled to transducer 34 by displacing the airway adapter in the direction indicated by arrow 205 in FIGS. 15 and 16 with the airway adapter center section 48 sliding into a complementary recess 206 defined by recess elements 207 and 208 in the side walls 122 and 126 of transducer casing components 108 and 110 (see FIG. 4) until a flange 208a on the airway adapter center section 48 contacts transducer casing 106. As airway adapter 36 slides into transducer 34, the flat back side 209 of airway adapter thermal capacitor 78 comes into contact with the also flat, front side 210 of the heating system conductive base 192 in transducer 34. This provides intimate physical contact between the system conductive base 192 and the thermal capacitor 78, insuring efficient, uniform transfer of heat from the system conductive base 192 to the thermal capacitor 78.

This intimate contact is promoted and maintained by a compressible O-ring 211 installed in conductive base 192 circumferential groove formed by recess 204 between side wall elements 212 (FIG. 14) and 214 of transducer casing component side walls 122 and 126. The O-ring 211 lies between: (a) side wall elements 212 and 214 and, (b) a groove bounding lip 216 at the airway adapter 36 facing, front side 210 of the conductive base 192 and is compressed as airway adapter 36 slides into transducer 34 and as is suggested by arrow 217 in FIG. 16. The tendency of O-ring 211 to return from the compressed state shown in FIG. 16 to the unstressed state shown in FIG. 15 promotes the wanted intimate contact between the conductive base 192 and thermal capacitor 78 by biasing the conductive base 192 toward the thermal capacitor 78.

The dimensioning of conductive base 192 peripheral recess 204 relative to the thickness of transducer casing side wall elements 212 and 214 provides for relative movement between conductive base 192 and the transducer casing 106 in the arrow 217 direction. That movement compensates for any structural misalignments or variations in dimension between airway adapter 36 and transducer 34.

Turning now to FIGS. 2, 3, 5, and 6, it is critical to the performance of apparatus 30 that airway adapter 36 be oriented in the correct relationship to transducer 34 (shown in full lines in FIG. 3) rather than in the opposite relationship shown in phantom lines in the same figure. Incorrect assembly is precluded by stops 218 and 220 on transducer casing end wall 128 and complementary stops 222 and 224 on-airway adapter end section 52 (see FIG. 15). Any attempt to install airway adapter 36 in transducer 34 in the wrong, phantom line orientation results in the airway adapter stops 222 and 224 engaging transducer casing stops 218 and 220, preventing the airway adapter 36 from being coupled to the transducer 34.

Referring now to FIGS. 4 and 13, it was pointed out above that transducer 34 includes a PCB 116 on which various circuits and electrical components of the transducer operating systems are mounted. PCB 116 is supported in PCB guides 228 and 230 located at opposite sides of transducer casing 106 (the top and bottom sides of the transducer 34 with that system component oriented as shown in FIG. 13). Lower guide 228, as shown in FIG. 4, is made up of spaced apart lugs 232 and 234 in casing component 108 and lugs 236 and 238 in casing component 110. The distance between the lugs 232–234 and 236–238 is slightly greater than the width of PCB 116 so that the PCB 116 can be readily fitted into the PCB guides 228–230.

The upper guide PCB 230 essentially duplicates the lower guide 228. Those PCB guide segments in transducer casing component 110 are shown in FIG. 13 and identified by reference characters 239 and 240. These segments are duplicated in mirror image relationship in casing component 108.

Leads collectively identified by reference characters 241 and 242 extend through aperture 243 in transducer casing component 110 and are incorporated in the electrical cable 40 which connects the circuitry on PCB 116 to the hand held control and display unit 38.

Figure 17:
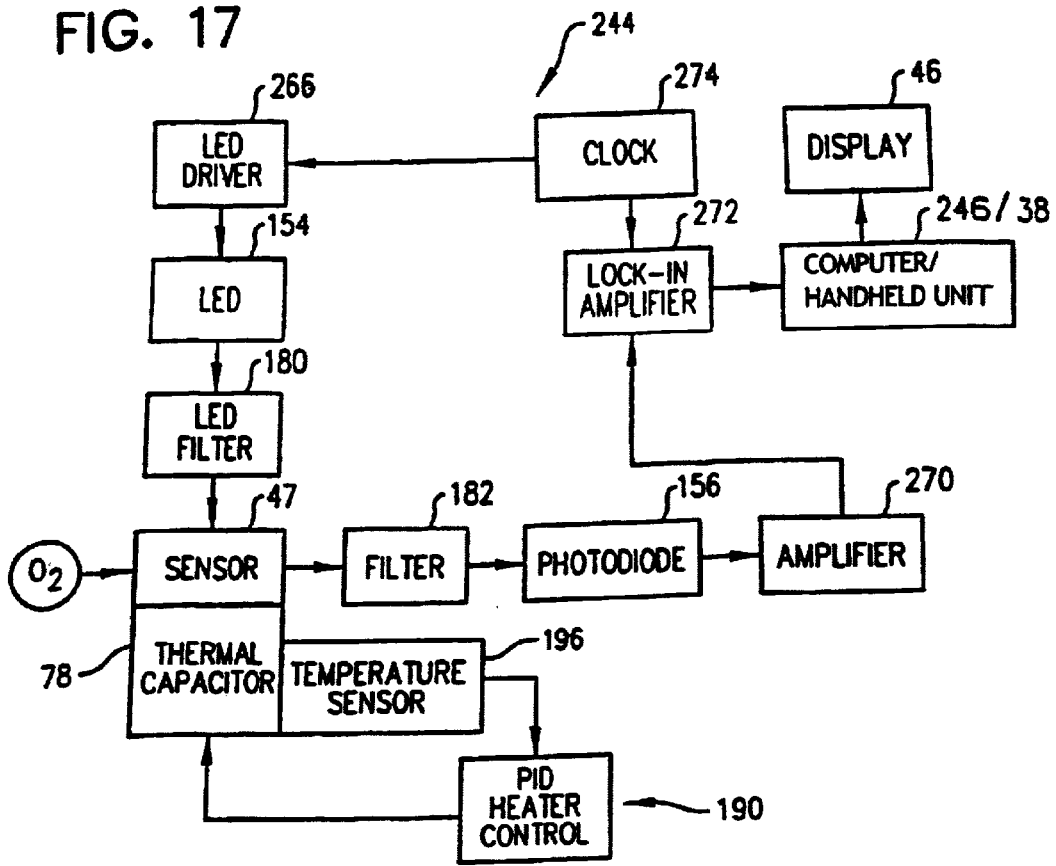
FIG. 17 shows, in block diagram form, the operating system of the FIG. 1 apparatus.

Referring still to the drawing, reference character 244 in FIG. 17 identifies the operating system of transducer 34. Also shown in FIG. 17 are LED 154, LED filter 180, thermal capacitor 78, conductive base 192 (FIG. 15), temperature sensor 196, photodiode data detector 156, and data detector filter 182. The display array 46 and data processing computer 246 of hand held unit 38 are also shown in block diagram in that figure.

Operating system 244 includes a conventional driver 266 for LED 154 and heater control 190 which is preferably of the PID (proportional-integral-differential) type. The heater control 190 accepts temperature data from sensor 196 and, based on the sensed temperature, controls the flow of current to the thick film resistive heater 194 of the sensor heating system 114 in transducer 34.

Operating system 244 also includes an amplifier 270 for the oxygen concentration indicative signal outputted by photodiode data detector 156 and a lock-in amplifier 272. The signal from the lock-in amplifier 272 is further processed in the computer 246 of display unit 38 and converted into a reading for display array 46. A clock 274 controls the operation of LED driver 266 and lock-in amplifier 272.

Figure 18:
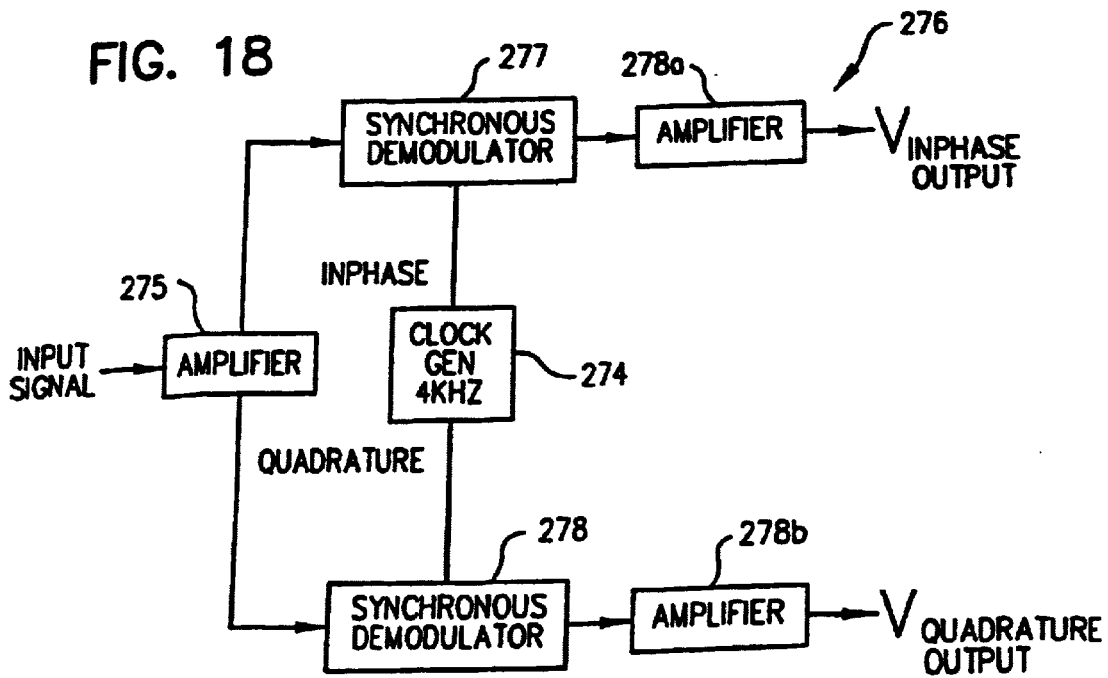
FIG. 18 is a block diagram of a lock-in amplifier circuit incorporated in the FIG. 17 operating system; the lock-in amplifier is employed to isolate from accompanying noise that component of the signal produced by a data detector in the transducer which is actually indicative of the concentration of oxygen in the gases being monitored.

The lock-in amplifier circuit shown in FIG. 18 and identified by reference character 276 possesses especially attractive and simple processing of the phosphorescence decay signals from oxygen sensor component 47. In the FIG. 18 circuit 276, a square or sine wave generated at a selected fixed frequency by clock generator 274 (FIG. 17) provides an input signal which is amplified by amplifier 275. This amplified frequency is used to modulate the light output of LED 154 and serves as a reference for lock-in amplifier 272. The lock-in amplifier 272 only detects signals at the same frequency as this reference, thereby rejecting all d.c. signals and nearly all signals at any other frequency. This enables detection of weak signals having a strength which is orders of magnitude below the level of all electronic noise in operating system 244.

The rise and decay times of the luminescence generated by the excited sensor component 47 cause the signal generated by data detector 156 to have a phase lag with respect to the wave form of original LED driver 266. Measurement of this phase lag is the equivalent of measuring the luminescence decay time, which is the oxygen-dependent parameter of interest. In the FIG. 18 lock-in amplifier circuit 276, second reference phase is generated at the same frequency as the first, but with a phase lag of exactly 90°. In each of the two synchronous demodulators 277, 278, and associated amplifiers 278a and 278b in the FIG. 18 circuit 276, the data signal is multiplied by one of these two phase references. This produces two resultant signals, which are the in-phase and quadrature components of the original signal from data detector 156. For a static signal, these two outputs are d.c. voltages. This is another advantage of lock-in amplification in that the signal processing circuitry needs to handle only the analog-to-digital conversion of two d.c., slowly varying voltages. The amplitude and phase of the signal is gotten by simple calculations from these two voltages as follows:

$$A=(V_I^2+V_Q^2)^{1/2}$$

$$\theta=\tan^{-1}(V_Q/V_I)$$

where:
  A=amplitude
  θ=phase angle
  VQ=quadrature voltage
  VI=in-phase voltage This detection scheme with its simplicity of operation is a significant feature of the present invention. Direct measurement of the decay times in the heretofore proposed microsecond range requires an electronic sampling system running at megahertz frequencies. In systems as disclosed herein, in contrast, optimization of phase detection occurs at much lower frequencies (ca. 5–25 kHz). That this is true is important because it greatly simplifies the electronic circuitry.

As discussed above, clock 274 provides a square or sine wave signal. This signal is used to produce a modulated light output from LED 154, which follows the driver 266 to which the clock 274 is coupled. The modulated light from the LED 154 excites sensor component 47 into luminescence. This luminescence (or phosphorescence) has a time decay which is dependent upon the oxygen concentration in the medium bathing sensor component 47. The light emitted by the luminescing sensor is detected by silicon PIN photodiode detector 156 where it is converted into a current, then amplified and sent to the inputs of the dual-channel lock-in amplifier 272. This current signal looks like the reference or driver wave form with a phase shift or delay proportional to the phosphorescence decay time. Two lock-in amplifier outputs, V (in-phase) and V (quadrature) are sampled by an analog to digital converter (not shown) in the computer 246 of hand held display unit 38. The amplitude and phase of the signal are then calculated by computer 246 from the two voltages.

In a calibration mode, the decay times or phase angles are measured as a function of standard calibration gases of known oxygen concentration, and the values are entered into a calibration file in the computer memory. For oxygen measurement, the lock-in voltages and resultant phase angles are collected and averaged in computer 246 and converted to oxygen levels using the calibration file and an interpolation or fitting routine. The calculated oxygen level is then displayed on the display array 46 of hand held display unit 38.

Figure 19:
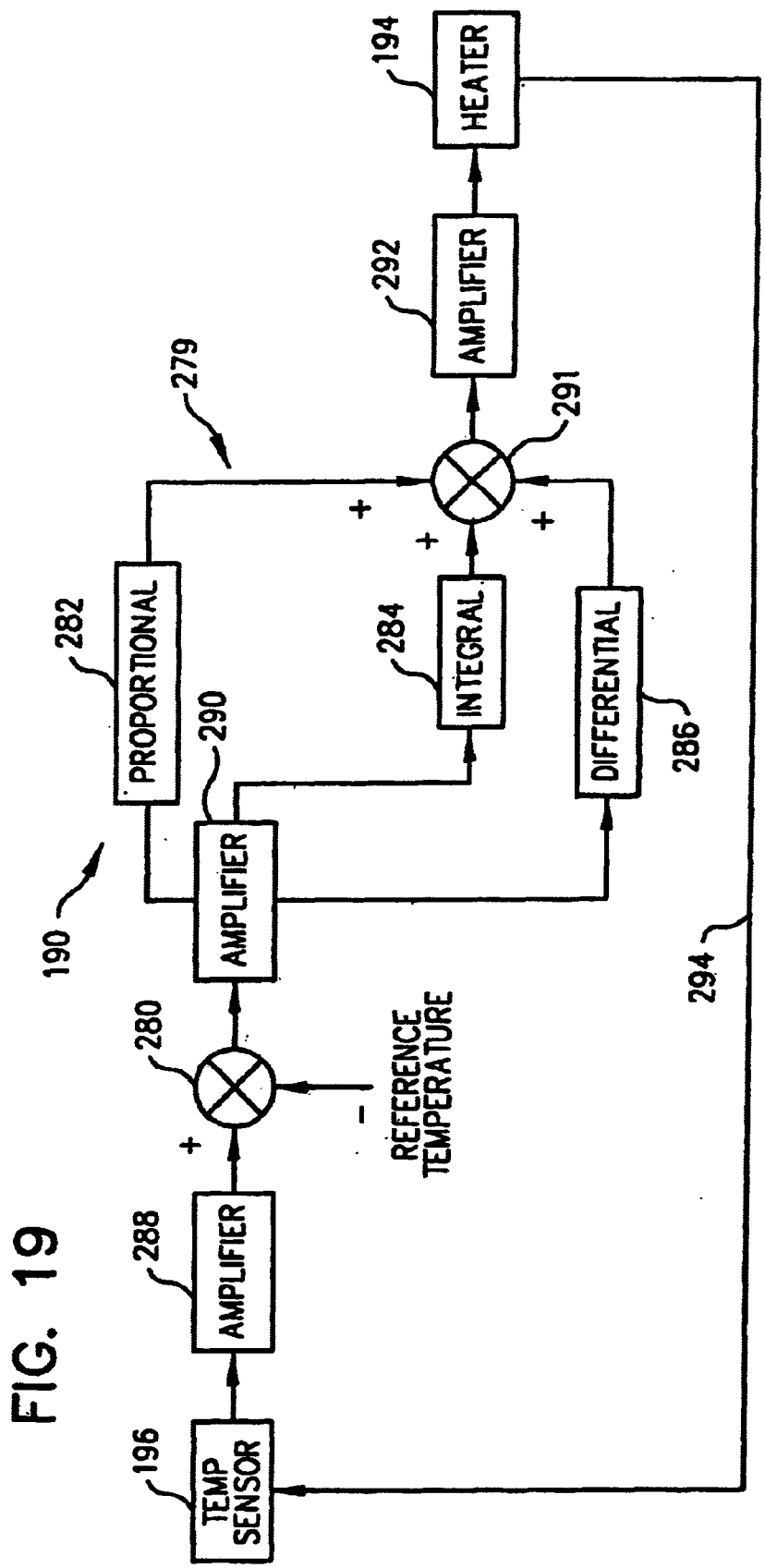
FIG. 19 is a block diagram of a heater control incorporated in the transducer; this control is employed in maintaining the sensor in the airway adapter at a constant operating temperature.

The heater control 190 for sensor heating system 114 is shown in more detail, albeit still in block diagram form, in FIG. 19. Sensor heater control 190 uses a proportional-integral-differential (PID) heater controller 279 for active temperature stabilization of thermal capacitor 78 and oxygen sensor component 47. To this end, the temperature of the heat sink (or heater base) 192 in transducer 34 as provided by the temperature sensor 196 mounted thereon is converted to a temperature indicative voltage input to the PID circuit. This voltage, amplified with amplifier 288, is compared within the circuit by a comparator 280 with a pot-settable voltage representing the temperature setpoint. Proportional, integral and differential comparisons of the sensed and setpoint temperature signals over time are developed by PID heater controller 279 as indicated by the boxes labeled 282, 284, and 286. More specifically, the temperature voltage is amplified (amplifier 288) and the reference temperature voltage is subtracted from it. The resultant temperature error voltage is amplified (amplifier 290) and split into three paths: Proportional (P), Integral (I), and Differential (D).

The Proportional path represents the temperature error magnitude, the Integral path represents the integral of the temperature error over time, and the Differential path represents the rate of change of the temperature error. The three paths are summed by a summing junction 291 at the input of amplifier 292. The amplifier output drives the resistance heater 194 which is also mounted on conductive base 192.

Thermal feedback is provided by conductive base 192 (FIG. 13) which is chosen for good thermal conductivity. Tuning the circuit for the thermal characteristics of conductive base 192 and heater 194 results in an operating voltage which, amplified by amplifier 292, is aggressively applied to the resistive heater 194 in contact with conductive base 192 whenever a decrease in temperature is detected. Likewise, the PID heater control 190 quickly reduces the rate of heating as the conductive base temperature approaches the set temperature and cuts off heating when the two temperatures match. Since the thermal sink (conductive base 192) is held well above ambient temperature, cessation of heating results in the onset of rapid cooling. This is immediately detected by PID heater controller 279 by virtue of the thermal feedback from heater 194 to temperature sensor 196 as indicated by line 294 in FIG. 19. The result is the application of frequent pulses of heat to conductive base 192, stabilizing it and sensor component 47 within a narrow range (one or two tenths of a Celsius degree) near the setpoint.

Heat transfer from conductive base 192 by conduction is also instrumental in keeping moisture from condensing on-airway adapter window 74. This is significant because moisture condensed on window 74 can adversely affect the accuracy of the oxygen concentration measurement made by apparatus 30 to a significant extent.

The three-fold way in which PID heater controller 279 "decides" to respond to temperature change allows the heater control system 190 to respond rapidly to conditions such as those appurtenant to large gas flows, resulting in only minimal variation in the conductive base 192 and sensor component 47 temperature. Even with the sizeable temperature dependence of the sensor component 47, the temperature control just described responds to the sensor temperature changes so fast as to suit it for breath-by-breath analysis applications of the present invention.

In more detail, the PID heater controller 279 works by having a temperature setpoint, Ts, represented by a corresponding voltage. The measured temperature T is represented by a voltage developed by temperature sensor 196 which may be a thermocouple or thermistor, and T is compared to Ts by comparator 280 as described above. PID heater controller 279 applies a heating voltage proportional to the temperature difference as follows:

$$P = GpX\ (Ts-T)$$

where:
P is the heating voltage,
Ts-T is the difference between the detected temperature and the temperature setpoint, and
Gp is the proportional gain of the circuit.

This proportional heating approach gives more precise temperature control than simple on-off heating, but is still not generally sufficient for tight temperature control at temperatures near the setpoint temperature. This is because, as T approaches Ts, the proportional difference is small. At small gains, very little heat is delivered to conductive base 192, and the time to heat the base to Ts is long or even infinite. Increasing Gp, the gain, to decrease the heating time has the effect of causing heating overshoot. This, in turn, causes instability of the sensor temperature as the system must turn off and cool by natural heat loss. The overshoot at high gain is remedied in part by adding the differential temperature control circuit. This offsets the tendency of the heater control 190 to overshoot the setpoint temperature by damping the heating when a high rate of change of Ts-T is detected. Proportional heating always tends to settle below the setpoint, however. To correct this, the signal is designed to bootstrap the system to a temperature close to the setpoint temperature. Specifically, the integral circuit integrates the difference between the setpoint and measured temperatures and applies heat to force the integral near zero. This effectively counteracts the residual temperature difference from the proportional circuit, resulting in the sensor setpoint temperature T being maintained very near, if not at, the setpoint temperature Ts.

Resolution of small differences in oxygen partial pressures places high demands on instrument performance in a luminescence-quenching system. This is particularly true for higher oxygen concentrations. The luminescence quenching-based process produces a signal over a high dynamic range; in going from 0 to 100% oxygen, the signal amplitude halves several times over. Likewise, the decay time decreases by a decade or more. Phase-sensitive or lock-in detection which is preferred and described above is run at a detection frequency that is optimized for the transition time being detected, making it possible to measure small differences in the transition time in systems employing the principles of the present invention and the luminescence decay time. Phase optimization occurs at a combination of frequency, $f_1$ and decay time, $t_1$ where the detected phase angle is 45°. When the decay time changes ten-fold, the optimal detection frequency also changes ten-fold. Over any such measurement range, choice of one particular detection frequency may, therefore, seriously degrade the resolution of the oxygen concentration signal.

There is additional negative impact from the large change in amplitude of the signal. Generally, it is desirable to operate stages of the lock-in amplifier circuit 276 (FIG. 18) at high gain so that any noise entering the system will have minimal effect on the signal-to-noise ratio. Optimization of the widely-varying signal presents a problem. In order to have a sizeable magnitude of the much-diminished signal at high oxygen concentrations, the low-oxygen signal is often "offscale" of a device such as an analog-to-digital converter. Conversely, with a low-oxygen signal employed full scale, the high-oxygen signal is small enough to suffer degraded resolution.

Figure 21:
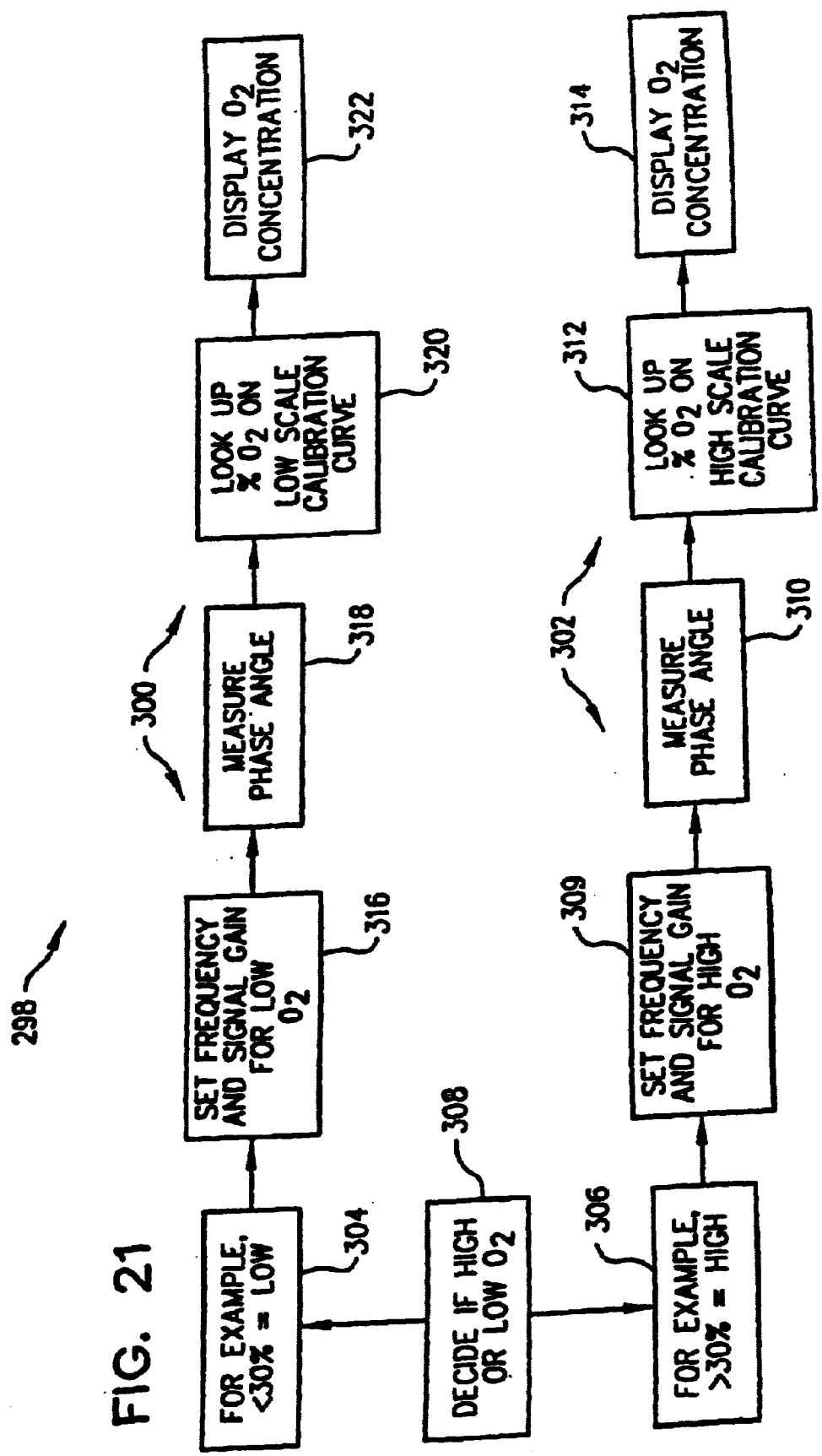
FIG. 21 is a block diagram showing two different protocols for processing the detector-generated signal after that signal has been processed by the transducer electronics; one protocol is employed if there is a high concentration of oxygen in the gases being monitored, and the second protocol is employed if the oxygen concentration is low.

A signal processing system of the character shown in FIG. 21 and identified by reference character 298 solves this problem by providing a dual measurement scale to enhance the accuracy of measurement of oxygen concentration indicative signals of widely varying amplitude and decay time.

As indicated by signal processing branches 300 and 302 in FIG. 21, two signal modulation frequencies are chosen, one such that the phase angles of signals for a low oxygen range will be as close as possible to 45°. The second modulation frequency is chosen to meet the same criterion for the phase angles of signals indicative of high oxygen concentrations. This provides at both high and low concentrations of oxygen in the gases being monitored a signal which has a high degree of resolution yet can be handled by a conventional analog-to-digital converter.

As suggested by boxes 304 and 306 in FIG. 21, low oxygen concentrations can, in applications of the present invention involving breath-by-breath monitoring, typically be defined as those with less than 30 percent oxygen and high oxygen concentration ranges as those having more than 30 percent oxygen.

The signal processing system 298 of oxygen monitoring apparatus 30 is switched between the high and low ranges (decision box 308) manually or automatically in response to the detection of a parameter such as decay time.

With the signal processing system switched to the LOW range setting (box 316), the phase of the data signal generated by data detector 154 is measured as indicated by box 318. Next, the oxygen concentration corresponding to the measured phase angle is looked up as from a digitally stored calibration curve (box 320); and the concentration is shown (box 322) as on the display array 46 of display unit 38.

Equivalent steps are employed if the oxygen concentration being measured is in the HIGH range and the signal processing circuitry is manually or automatically switched to the high range frequency modulation (reference character 309) setting. The phase angle of the data detector generated, oxygen concentration indicative signal is measured (box 310); and the corresponding oxygen concentration is looked up (box 312) and shown on display array 46 of display unit 38 (box 314).

A similar scheme can be employed for an amplitude scale. An automatic gain control (AGC) circuit may be used to keep the signal level at a constant amplitude, or a dual gain setting can be established in conjunction with the frequency scale.

Figure 20:
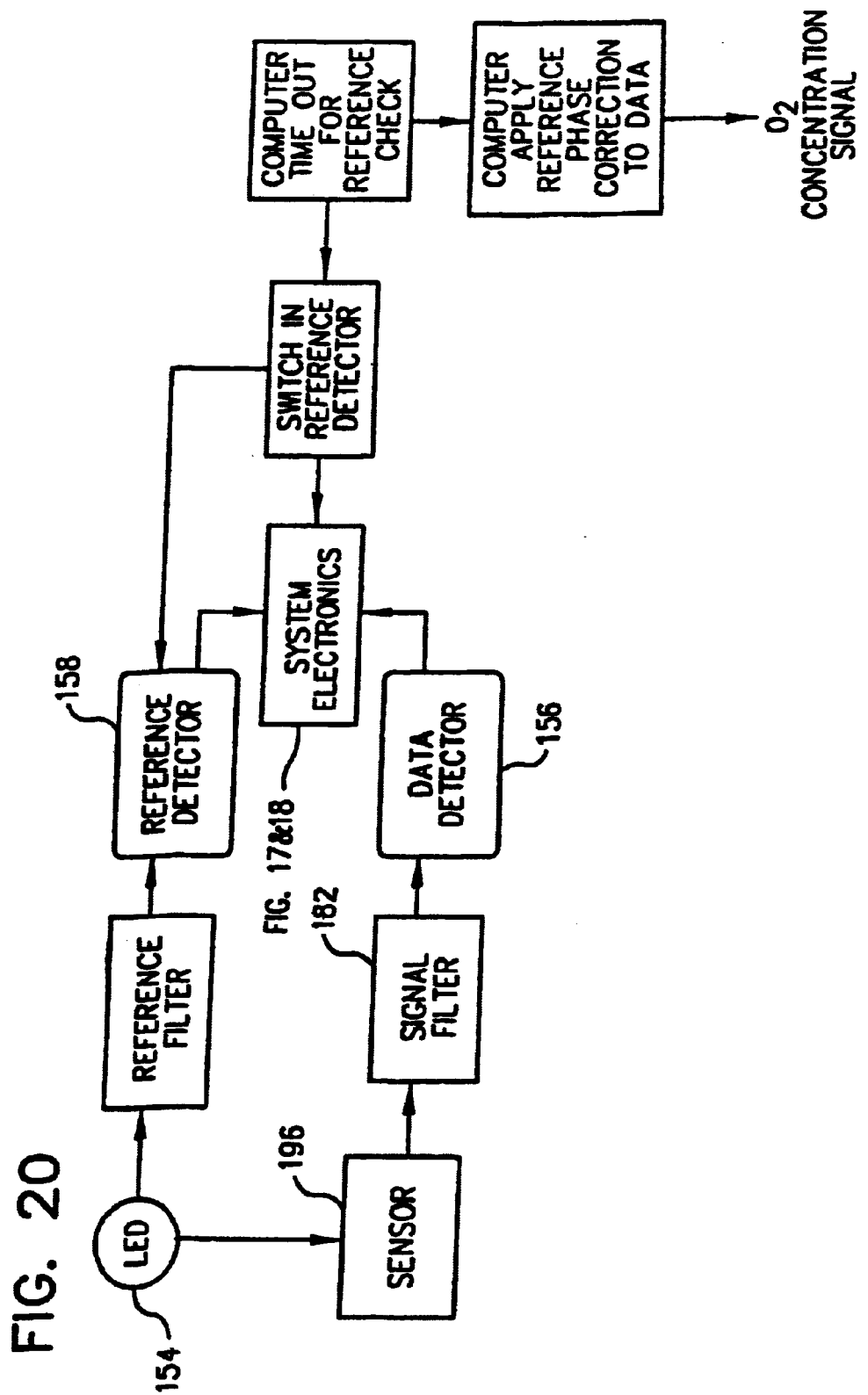
FIG. 20 is a block diagram showing how the signal propagated from the data detector of the FIG. 4 transducer is converted to a signal indicative of the concentration of oxygen in the gases being monitored.

It will be remembered that the exemplary oxygen concentration monitoring apparatus 30 disclosed herein employs both a data detector 156 and a reference detector 158. Using a reference signal to periodically calibrate data detector 156 increases the accuracy of the oxygen value displayed by unit 38. As shown in FIG. 20, the reference detector 158 is switched into the signal processing circuit with the computer 246 switching from a data measuring mode to a calibration mode while reference detector 158 is active. The reference signal is processed through the lock-in amplifier circuit 276 with the processed signal being transmitted to computer 246 to switch the computer to its "time out for reference check mode." The reference detector signal is also sent directly to computer 246 to provide a signal which the computer can employ to apply an appropriate correction to the signal generated by data detector 156.

Figure 22:
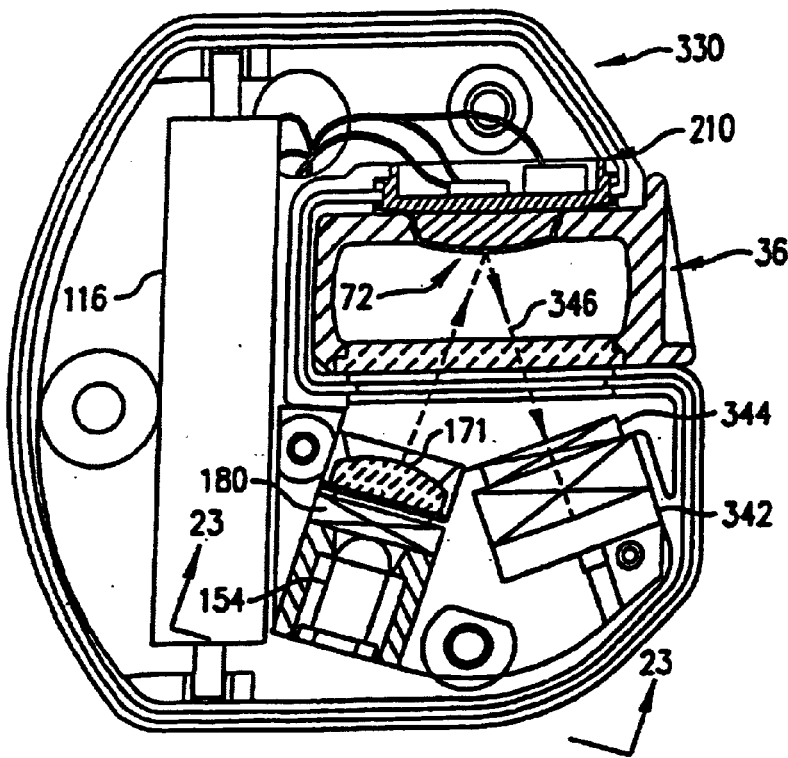
FIG. 22 is a view, similar to FIG. 13, of a second oxygen concentration monitoring transducer employing the principles of the present invention and consisting of an airway adapter and a transducer with dual light sources and a single detector.
Figure 23:
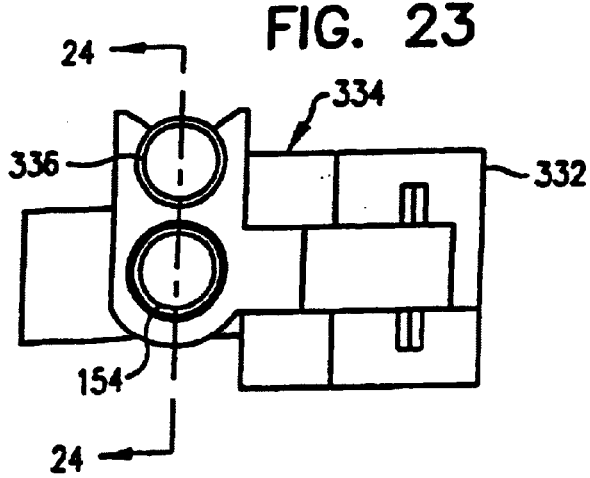
FIG. 23 is a front view of an optical subassembly employed in the FIG. 22 transducer and consisting of an optical platform to which the dual light sources and detector are mounted.
Figure 24:
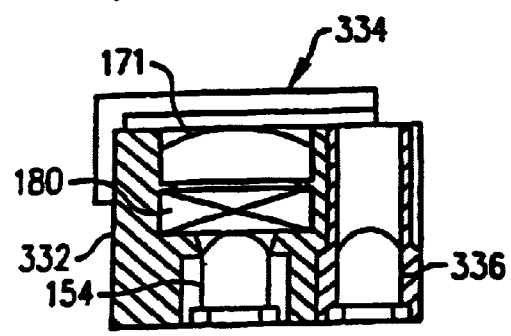
FIG. 24 is a section through the optical assembly of FIG. 23, taken substantially along line 24–24.

The advantages of basing an oxygen concentration indicative signal on a data signal corrected by a reference signal can alternatively be realized by using data and reference light sources and a single detector. A transducer employing this scheme is illustrated in FIGS. 22–24 and identified by reference character 330.

For the most part, transducer 330 is like the transducer 34 described above. Components of the two transducers which are alike will accordingly be identified by the same reference characters.

Transducer 330 differs from transducer 34 in one significant respect in that the platform 332 of the transducer 330 optical assembly 334 is configured to support a second reference light source 336 such as an orange red, or ultraviolet LED. The two LEDs 154 and 336 are mounted in side-by-side relationship in platform 332.

Transducer 330 also differs significantly from transducer 34 in that it employs only a single detector 342 which supported from platform 332 in the optical path 346 between sensor component 47 (FIG. 5) and the detector 342. Detector 342 is a data detector and generates a signal indicative of the concentration of oxygen in the gases being monitored.

Light from reference LED 336 does not excite the luminescable composition in sensor component 47 but is reflected from the sensor component 47, passing through filter 344 to photodetector 342 and producing an electrical signal related to the intensity of the light emitted from LED 336. The signal so obtained may be used as a reference phase correction for drifts in the electronic system. The second LED 336 may be switched on to provide a reference or calibration point from time to time, as desired, or may be switched on for regular, short intervals to provide a nearly continuous automatic reference.

The exemplary oxygen concentration monitoring apparatus 30 shown in FIG. 1 of the drawings and discussed above is of the mainstream, on-line type. However, the principles of the present invention can equally well be employed in sidestream sampling systems. One representative system of this character is shown in FIGS. 25–27 and identified by reference character 350.

System 350 includes a nasal cannula 352, an oxygen concentration monitor 354 embodying the principles of the present invention, absolute and differential pressure transducers 356 and 358, a barometric pressure port 360, a vacuum pump 362, and a damping chamber 364.

Nasal cannula 352 (FIG. 26) is conventional. It includes tubing 366 which fits over the head of a patient 368. An insert 370 in the tubing has nipples (one shown and identified by reference character 374) that fit into the patient's nostrils. The nasal cannula is connected as by tubular fitting 376 to a flexible Nafine drying tube 378. The drying tube removes moisture from gases exhaled by patient 368, thereby eliminating errors which that moisture might cause. At the far end of the tube is the female component 380 of a conventional Leur fitting.

Figure 25:
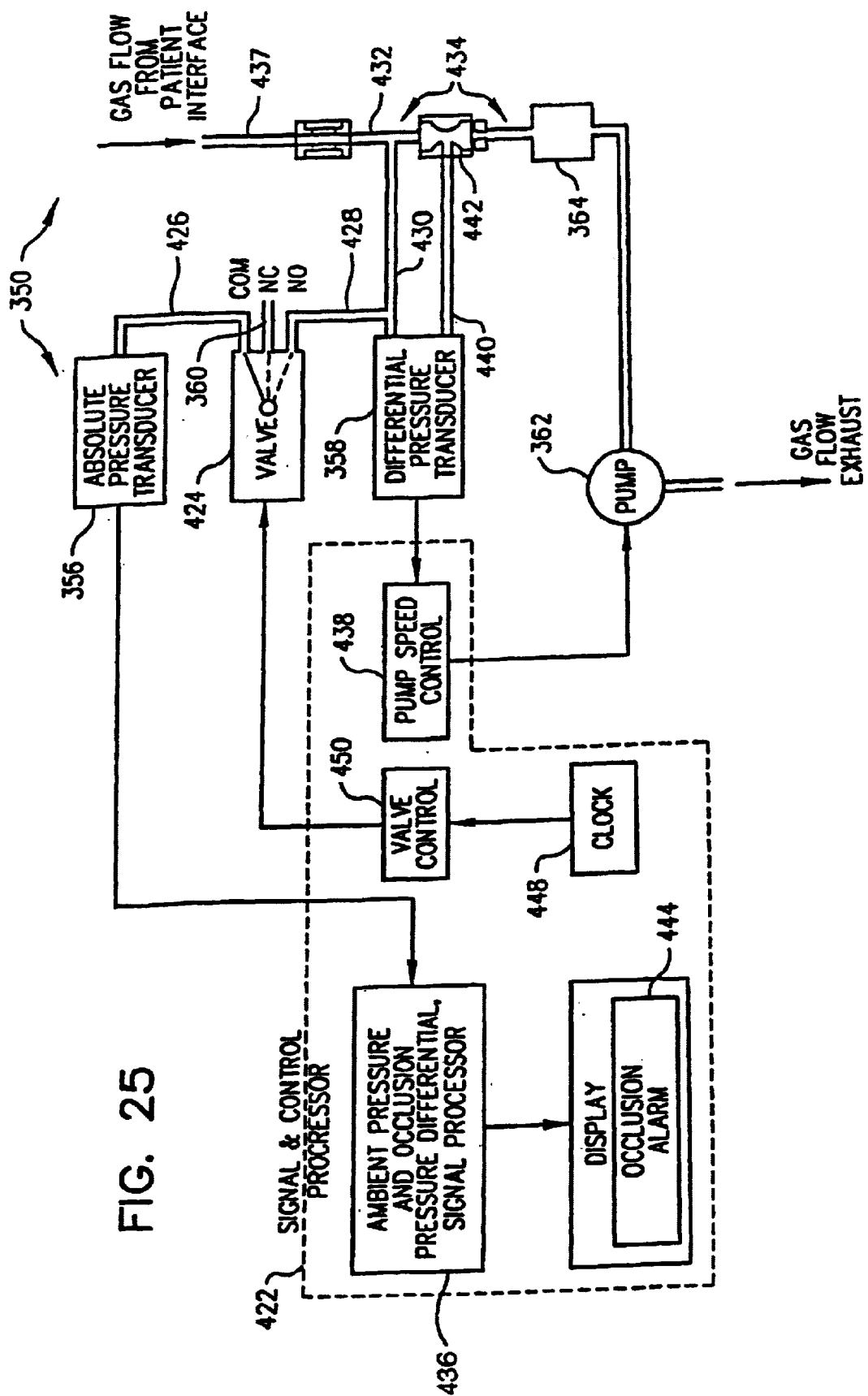
FIG. 25 shows a sidestream sampling, oxygen concentration monitoring system employing the principles of the present invention.
Figure 26:
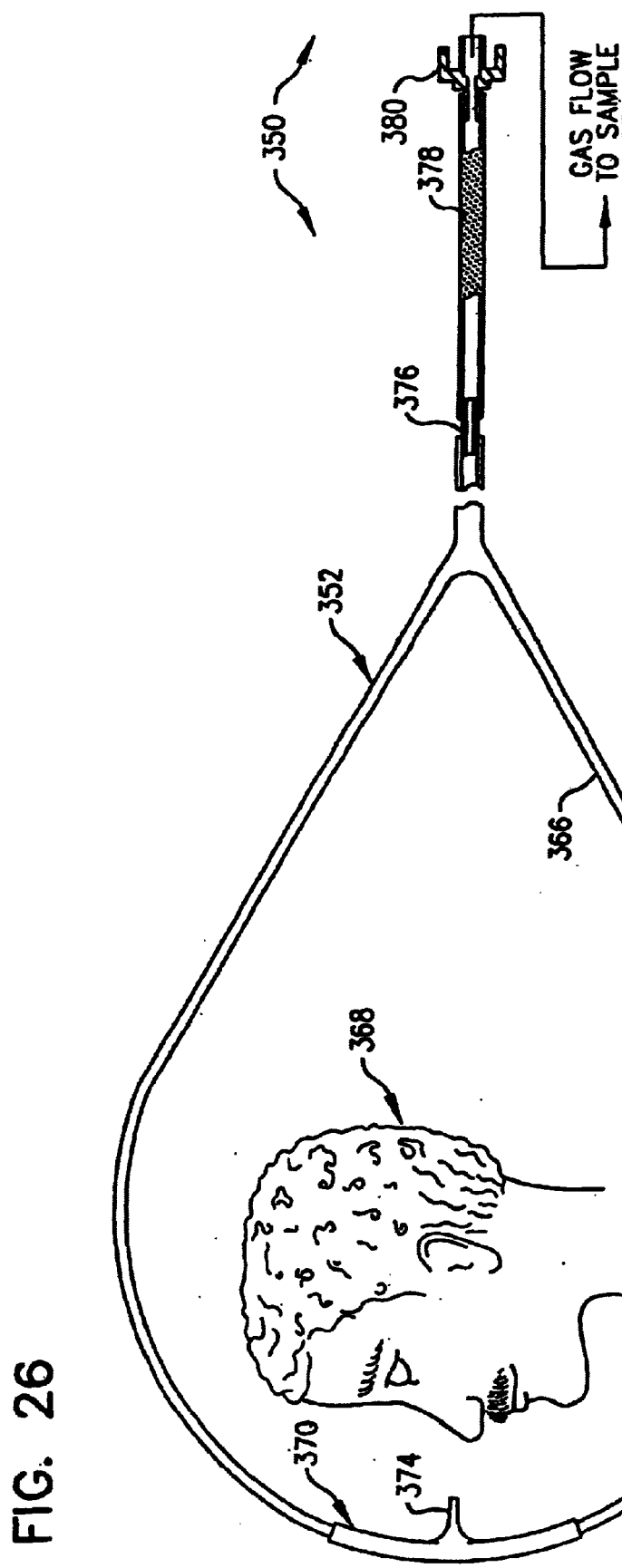
FIGS. 26 illustrates a nasal cannula component of the exemplary FIG. 25 system.
Figure 27:
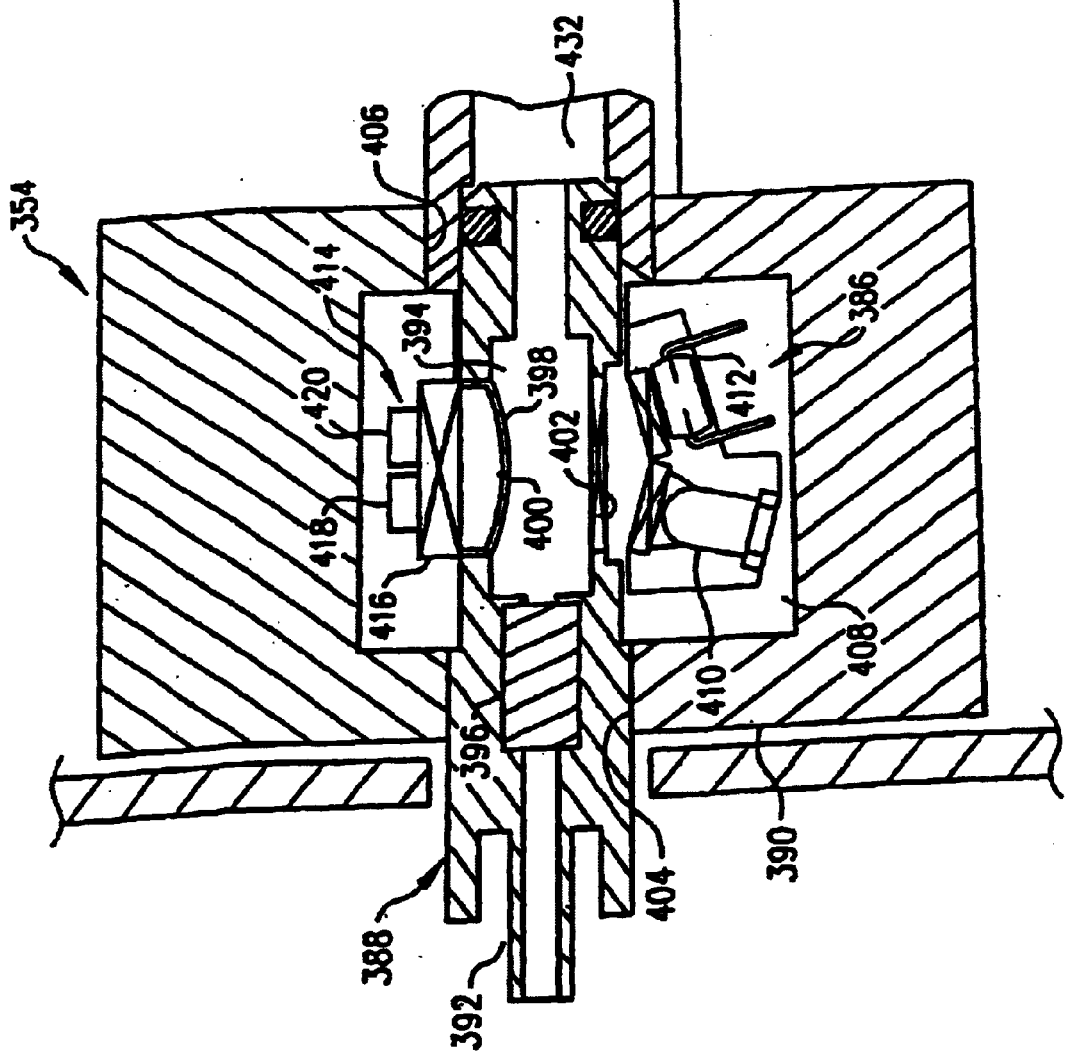
FIG. 27 shows, in some detail, a sampling cell and a transducer of the FIG. 25 system; this figure also shows in block diagram form a signal processing and control unit of the system.

Referring now specifically to FIGS. 25 and 27, the oxygen concentration monitor 354 of sidestream sampling system 350 includes an oxygen concentration signal generating transducer 386 and a removable sampling cell 388. The sampling cell 388 has a casing 390 which terminates in a male Leur fitting 392 which complements the female component 380 of that fitting shown in FIG. 26. The two Leur fitting components are plugged together to establish fluid communication from the patient 368 being monitored through nasal cannula 352 and drying tube 378 to a flow passage 394 extending from end-to-end through sampling cell 388. A filter 396 is installed in flow passage 394 to remove any remaining moisture and other foreign material from the patient's exhaled gases before those gases are monitored for oxygen content.

Mounted in the casing 390 of transducer 386 is a luminescable oxygen sensor 398 supported by a thermal capacitor 400. Opposite the sensor/thermal capacitor assembly is a transparent window 402. Those components are akin to the correspondingly named components of the system shown in FIG. 1 and will accordingly not be described further herein.

Referring still primarily to FIGS. 25 and 27, the casing 390 of transducer 386 has aligned apertures 404 and 406 with sampling cell 388 extending through those apertures. Housed in a compartment or cavity 408 in transducer casing 390 are a LED light source 410, a data detector 412 for light emitted from the sensor 398 of sample cell 388, and a sensor heating system 414 which cooperates with sampling cell thermal capacitor 400 to keep oxygen concentration sensor 398 at a constant temperature.

Heating system 414 includes a conductive heating element 416, a resistance heater 418, and a temperature sensor 420. The just-named components are like those employed in the oxygen monitoring apparatus 30 discussed above, and they are mounted in transducer casing 390 in much the same manner as the components of the corresponding on-line transducer 34. Consequently, and in the interest of avoiding unnecessary repetition, the just-identified internal components of transducer 386 will not be further described herein.

As is the case with an on-line system such as shown in FIG. 1, the electrical signals generated by the data detector 412 of transducer 386 are transmitted to a control/signal processing unit, in this case identified by reference character 422 and shown in FIGS. 25 and 27. Functions and the capabilities of unit 422 are also identified in FIG. 27.

Referring again to FIG. 25, an operator utilizing sidestream sampling system 350 for the first time operates a switch (not shown) to apply electrical power to the system. This results in a three-position valve 424 being moved to the NO position to equilibrate system 350 with barometric atmospheric pressure through lines 426, 428, and 430 and barometric pressure port 360 and to provide a barometric pressure value and a flow pressure differential. The just-identified lines provide a flow path 434 between barometric pressure port 360 and: (1) absolute pressure transducer 356, (2) differential pressure transducer 358, and (3) a sidestream sampling line 437. The sampling line continues the flow path from the sampling cell 388 of oxygen concentration monitor 354 to: (a) vacuum pump 362, and (b) damping chamber 364. The barometric and flow pressure differential values are stored in control/signal processor control monitor 422 and employed as reference during the operation of system 350.

After the reference pressure is stored, valve 424 is moved to the NC position. This applies atmospheric pressure to the absolute pressure transducer 356, which transmits a signal indicative of the barometric pressure to monitor 354. As just suggested, this pressure is utilized as a reference in the operation of sidestream sampling system 350.

During the operation of system 350, valve 424 is maintained in the COM position. This connects absolute pressure transducer 356 and differential pressure transducer 358 to sidestream sampling line 437 through lines 426, 428, 430, and 432. Differential pressure transducer 358 is also connected to the sidestream sampling line 437 by line 440 and orifice 442. This applies two different pressures across differential pressure transducer 358, resulting in the differential pressure transducer 358 having an output which represents the rate of flow of the gases being monitored along flow path 434.

With pressure transducers 356 and 358 connected to sidestream sampling line 437, vacuum pump 362 is operated. The motor (not shown) of vacuum pump 362 is voltage controlled by a loop that includes differential transducer 358 and a pump speed control 438, such as a computer processor operating under instructions of a pump speed feedback program, in communication with differential pressure transducer 358, such that a uniform flow of gas is maintained through the sampling cell 388 of oxygen concentration monitor 354 while the gases exhaled by a patient into nasal cannula 352 are being monitored.

At the same time, the pressure in sampling cell 388 is measured by absolute pressure transducer 356 with the pressure value being compared to the stored reference value. During oxygen concentration monitoring operation of system 350, absolute pressure transducer 356 continuously monitors the pressure in sidestream sampling line 437 with the current pressure values being compared with the stored value by way of a processor 436 in communication with absolute pressure transducer 356. This ensures that system 350 is operating within parameters which provide an accurate measurement of oxygen concentration by making it possible to almost instantaneously identify problems which might affect the accuracy of the oxygen concentration because such problems will affect the pressure in flow path 434. By way of example only, such problems include a dislodgment of nasal cannula 352 and a partial blockage of sampling cell 388. An occlusion alarm 444 (see FIG. 25) on control/signal processor control monitor 422 is activated if an occlusion is detected.

Systems employing the principles of the present invention may be employed in situations where the ambient pressure changes. For example, the system might be used to monitor a patient being transported by helicopter to a medical facility. As the helicopter rises, the ambient pressure drops. By periodically checking the ambient pressure, one can insure that the pressure in system 350 is compared to the current ambient baseline pressure, insuring that occlusions and other problems are detected while false alarms are avoided. To this end, the clock 448 shown in FIG. 25 periodically causes valve control 450 to shift valve 424 to the NC position to obtain an updated reference pressure.

It is important in making an accurate oxygen concentration measurement of the gases flowing through sidestream sampling cell 388 to have a constant rate-of-flow through the sampling cell 388. Variations in the flow rate would cause inaccuracies in oxygen concentration measurement of the gases being monitored through the sampling cell. Flow rate variations are detected by differential pressure transducer 358 which applies appropriate corrections to pump speed control 438. The pump is thereupon speeded up or slowed down to the extent necessary to keep the flow rate constant.

With pump 362 running, the system is zeroed for oxygen content by circulating air from the ambient surroundings through system sampling line 437 until the system pressure stabilizes. With this accomplished, system 350 is initialized and monitoring of the oxygen concentration in the exhalations of patient 368 can proceed.

During the determination of the patient's oxygen concentration, damping chamber 364 and an orifice 446 in sampling line 437 cooperate to dampen the unavoidable oscillations in the back pressure of vacuum pump 362. This minimizes variations in the pressure of gases flowing through sidestream sampling line 437 and sampling cell 388, minimizing, if not eliminating, the adverse effects which such pressure variations might have on the accuracy of the oxygen concentration indicative signal generated by oxygen concentration monitor 354.

At the conclusion of the oxygen concentration monitoring process, power is removed from system 350. The system is then readied for the next procedure by flushing the system 350 and/or replacing sampling cell 388. The oxygen concentration monitoring process can also be interrupted and a sampling cell replaced at any time that an occlusion in the cell is detected.

The invention may be embodied in many forms without departing from the spirit or essential characteristics of the invention. The present embodiments are therefore to be considered in all respects as illustrative and not restrictive. The scope of the invention is indicated by the appended claims rather than by the foregoing description, and all changes which come within the meaning and range of equivalency of the claims are therefore intended to be embraced therein.

What is claimed:

1. A method of producing an oxygen concentration monitoring sensor, the method comprising the steps of:
    forming a solution of a luminescable composition in an organic solvent;
    effecting the swelling of a matrix which comprises a film of hydrophobic polymer including a plurality of micropores in communication with an exterior thereof;
    bringing the solution of luminescable composition in contact with the film so that the solution penetrates into the swollen film; and
    removing the organic solvent such that the microporous hydrophobic polymer shrinks and traps at least a portion of the luminescable composition.

2. A method as defined in claim 1, wherein effecting swelling of the matrix comprises introducing the film into a bath of a swelling agent.

3. A method as defined in claim 2 which includes the acts of, after the film is introduced into the bath of swelling agent:
    introducing the solution of luminescable composition into the bath to effect the penetration of the luminescable composition into the film; and
    removing the impregnated film from the bath and then drying the film to trap the luminescable composition in the film.

4. The method of claim 1, wherein effecting the swelling of a matrix comprises effecting the swelling of the matrix so that the pores in the film of hydrophobic polymer allow the luminescable composition to be molecularly dispersed in the matrix.

5. A method as defined in claim 1, wherein removing the organic solvent comprises drying the film after bringing the solution of luminescable composition in contact with the film.

6. A method as defined in claim 1, in which the film has a thickness in the range of 5–20 $\mu$m and a pore size in the rate of 0.1 to 10 $\mu$m.

7. A method as defined in claim 1 in which the polymer is: a silicone, a polycarbonate, a polystyrene, a polymethyl methacrylate, a polyvinyl chloride, a polypropylene, a polyester, or an acrylic copolymer.

8. A method as defined in claim 1 in which the polymer is a track etched polycarbonate.

9. A method as defined in claim 1 in which the luminescable composition is an organometallic complex having a 300–700 $\mu$m absorption band and a 500–1000 $\mu$m emission band.

10. A method as defined in claim 1 in which the luminescable composition is a fluorinated porphyrin.

11. A method as defined in claim 10 in which the luminescable composition is selected from the group consisting of palladium meso-tetraphenyl porphine, platinum mesotetraphenyl porphine, palladium meso-tetra(perflouro) phenyl porphine, and platinum meso-tetra(perflouro) porphine.

12. A method as defined in claim 1 in which the organic solvent is hexane, a petroleum ether, toluene, methylene chloride, trichlotoethylene, xylene, tetrahydrofuran, dioxane, isopropyl alcohol, or butanol.

13. A method as defined in claim 1 which comprises the step of modifying at least one characteristic of the sensor by applying a polymeric overcoating to the film.

14. A method as defined in claim 13 in which said overcoating is provided by applying a dispersion or solution of said polymer to an exposed surface of the sensor.

15. A method as defined in claim 1 in which the overcoating is provided by bonding a film of the polymer to an exposed surface of the sensor.

16. A method as defined in claim 1 in which the solvent has the capability of fusing two of the matrices into a single lamina with the luminescable composition embedded therein.

* * * * *